US011867709B2

(12) United States Patent
Rousseau

(10) Patent No.: US 11,867,709 B2
(45) Date of Patent: *Jan. 9, 2024

(54) SYSTEM FOR CONVEYING SUPPORTS FOR CONTAINERS FOR BIOLOGICAL LIQUID SAMPLES, AND AUTOMATIC ANALYSIS SYSTEM COMPRISING SUCH A CONVEYING SYSTEM

(71) Applicant: ARTEION, Paris (FR)

(72) Inventor: Alain Rousseau, Paris (FR)

(73) Assignee: ARTEION, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/557,641

(22) Filed: Dec. 21, 2021

(65) Prior Publication Data
US 2022/0113326 A1 Apr. 14, 2022

Related U.S. Application Data

(63) Continuation of application No. 16/071,825, filed as application No. PCT/FR2017/050123 on Jan. 20, 2017, now Pat. No. 11,237,181.

(30) Foreign Application Priority Data

Jan. 25, 2016 (FR) .................... 16/50553

(51) Int. Cl.
G01N 35/04 (2006.01)
G01N 33/487 (2006.01)
G01N 35/00 (2006.01)

(52) U.S. Cl.
CPC ........... *G01N 35/04* (2013.01); *G01N 33/487* (2013.01); *G01N 35/00732* (2013.01); *G01N 2035/0465* (2013.01); *G01N 2035/0489* (2013.01)

(58) Field of Classification Search
CPC ............... G01N 35/04; G01N 33/487; G01N 35/00732; G01N 2035/0465; G01N 2035/0489
(Continued)

(56) References Cited

U.S. PATENT DOCUMENTS 4,113,436 A * 9/1978 Werder ............... G01N 35/021
436/98
7,338,803 B2 * 3/2008 Mizzer ............... G01N 35/1081
422/63
(Continued)

FOREIGN PATENT DOCUMENTS

CN 101135695 A 3/2008
CN 101470125 A 7/2009
(Continued)

OTHER PUBLICATIONS

English Translation of Japanese Office Action for Application No. 2018-538646; dated Jan. 5, 2021; 5 Pages.
(Continued)

Primary Examiner — Marrit Eyassu
(74) Attorney, Agent, or Firm — CANTOR COLBURN LLP

(57) ABSTRACT

The conveying system includes a support guide element defining a guide track, the support guide element being configured to receive a containers support and guide said containers support in translation along the guide track; and a self-propelled conveying carriage displaceable along a conveying track extending along the support guide element, the self-propelled conveying carriage comprising a drive element movably mounted between at least one drive position in which the drive element is configured to transmit a drive movement to the containers support so received on the support guide element, and a release position in which the drive element is configured to release the containers support,
(Continued)

the self-propelled conveying carriage being configured to displace the containers support in translation along the guide track when the drive element is in the drive position and the self-propelled conveying carriage is displaced along the conveying track.

15 Claims, 10 Drawing Sheets

(58) Field of Classification Search
USPC .......................................................... 73/863
See application file for complete search history.

(56) References Cited

U.S. PATENT DOCUMENTS

| | | | |
|---|---|---|---|
| 7,578,383 | B2 | 8/2009 | Itoh |
| 9,989,546 | B2 | 6/2018 | Rousseau |
| 10,094,846 | B2 | 10/2018 | Tokieda et al. |
| 11,391,750 | B2 | 7/2022 | Tokieda et al. |
| 2002/0021983 | A1 | 2/2002 | Comte et al. |
| 2003/0044319 | A1 | 3/2003 | Itoh |
| 2004/0096362 | A1 | 5/2004 | Barry et al. |
| 2004/0134750 | A1* | 7/2004 | Luoma, II ............... G01N 35/04 198/340 |
| 2005/0196320 | A1 | 9/2005 | Veiner et al. |
| 2005/0265896 | A1* | 12/2005 | Itoh ........................ G01N 35/04 422/65 |
| 2009/0162247 | A1* | 6/2009 | Tokieda ............... G01N 35/026 422/65 |
| 2011/0009238 | A1* | 1/2011 | Baba ....................... B61B 10/04 477/185 |
| 2011/0316713 | A1 | 12/2011 | Okubo |
| 2015/0014125 | A1 | 1/2015 | Hecht |
| 2015/0285829 | A1 | 10/2015 | Rousseau |
| 2016/0238625 | A1 | 8/2016 | Raicu et al. |
| 2018/0298426 | A1 | 10/2018 | Buse et al. |
| 2020/0166534 | A1 | 5/2020 | Rousseau |

FOREIGN PATENT DOCUMENTS

| | | | |
|---|---|---|---|
| JP | 2001174468 | A | 6/2001 |
| JP | 2001278409 | A | 10/2001 |
| JP | 2004217409 | A | 8/2004 |
| JP | 2008058202 | A | 3/2008 |
| JP | 2009150859 | A | 7/2009 |
| JP | 2009287269 | A | 12/2009 |
| JP | 2012184085 | A | 9/2012 |
| JP | 2013152244 | A | 8/2013 |
| JP | 2998057 | A1 | 5/2014 |
| WO | 2005093433 | A1 | 10/2005 |

OTHER PUBLICATIONS

International Search Report for Application No. PCT/FR2017/050123; International Application Filing Date: Jan. 20, 2017; dated Mar. 30, 2017, 4 pages.
Decision to Grant dated Jul. 13, 2021; JP Application No. 2018-538646; 5 pages (English translation included).
Decision to Grant dated Oct. 10, 2019; EP Application No. 17706555.4; 2 pages.
Examination reoprt No. 1 dated Apr. 13, 2021; AU Application No. 2017212756; 3 pages.
First Chinese Office Action dated Jun. 30, 2021; CN Application No. 201780007312.7; 14 pages (English translation included).
Intention to Grant dated Jul. 25, 2019; EP Application No. 17706555.4; 96 pages.
Notice of Acceptance dated Nov. 3, 2021; AU Application No. 2017212756; 3 pages.
Notification of Grant dated Mar. 3, 2022; CN Application No. 201780007312.7; 2 pages (English translation included).
Office Action dated Dec. 15, 2022; CA Application No. 3010672; 6 pages (non-English).
Opinion dated Oct. 18, 2016; FR Application No. 1650553; 4 pages (non-English).
Search Report dated Nov. 2, 2020; JP Application No. 2018-538646; 44 pages (English translation included).
Search Report dated Oct. 18, 2016; FR Application No. 1650553; 2 pages.
Written Opinion dated Apr. 6, 2017; PCT Application No. PCT/FR2017/050123; 12 pages (English translastion Included).

* cited by examiner

SYSTEM FOR CONVEYING SUPPORTS FOR CONTAINERS FOR BIOLOGICAL LIQUID SAMPLES, AND AUTOMATIC ANALYSIS SYSTEM COMPRISING SUCH A CONVEYING SYSTEM

CROSS REFERENCE TO RELATED APPLICATIONS

This application is a Continuation Application of U.S. application Ser. No. 16/071,825 filed on Jul. 20, 2018, which is a National Stage of PCT Application No. PCT/FR2017/050123 filed on Jan. 20, 2017, which claims priority to French Patent Application No. 16/50553 filed on Jan. 25, 2016, the contents each of which are incorporated herein by reference thereto.

TECHNICAL FIELD

The present invention concerns a conveying system configured to convey containers supports intended to support containers containing samples of a biological liquid, and an automatic analysis system for in vitro diagnosis comprising such a conveying system.

BACKGROUND

In a known manner, an automatic analysis system for in vitro analysis, also called automatic laboratory system, comprises:
- a plurality of containers supports intended to support containers containing samples of a biological liquid to analyze,
- a conveying system comprising:
  - a conveying unit configured to receive and convey containers supports according to a conveying track, the conveying unit generally including a conveyor belt or a magnetic conveying device,
  - a loading area configured to load containers supports on the conveying unit, and
- a plurality of analysis and/or measurement stations disposed along the conveying track, and intended to be supplied with containers supports by the conveying unit.

Although such an automatic analysis system considerably limits the tedious manipulations for an operator, it does not ensure a high conveying cadence and a high analysis cadence, in particular when a containers support must be conveyed between different analysis and/or measurement stations.

Furthermore, most known conveying systems present a high complexity in particular because of the presence of conveyor belts or of magnetic conveying devices, and this complexity is generally spread out over the entirety of the conveying systems. Hence, the costs of the known conveying systems are high, and sometimes higher than the costs of the analysis and/or measurement stations. Such a complexity of the conveying systems also induces laborious configurations and installations and a delicate maintainability, and may cause numerous potential failures.

In addition, in the event of a failure of the conveying unit, for example in the event of a failure of the drive mechanism of the conveyor belt or a wearing of the conveyor belt, the downtime of the automatic analysis system may turn out to be long and costly for an analysis laboratory.

BRIEF SUMMARY

The present invention aims at overcoming these drawbacks.

Hence, the technical problem at the origin of the invention consists in providing a conveying system which has a simple, economical and reliable structure, while ensuring a high conveying capacity, an optimized analysis cadence and a simple and rapid maintainability.

To this end, the present invention concerns a conveying system configured to convey containers supports intended to support containers containing samples of a biological liquid, the conveying system including at least:
- a support guide element defining a guide track, the support guide element being configured to receive a containers support and guide said containers support in translation along the guide track,
- a self-propelled conveying carriage displaceable along a conveying track extending along the support guide element, the self-propelled conveying carriage comprising a drive element movably mounted between at least one drive position in which the drive element is configured to transmit a drive movement to the containers support received on the support guide element, and a release position in which the drive element is configured to release the containers support, the self-propelled conveying carriage being configured to displace the containers support in translation along the guide track when the drive element is in the drive position and the self-propelled conveying carriage is displaced along the conveying track.

Such a configuration of the conveying system, and more particularly of the conveying carriage, enables a simple, easy and rapid conveyance of a containers support between loading and unloading areas and analysis and measurement stations, and thus ensures a high conveying and analysis cadence.

In addition, in the event of a failure of the conveying carriage, all it needs is to replace the latter with another conveying carriage, which ensures a short downtime of the conveying system, and therefore considerably limits the financial losses for the analysis laboratory.

Furthermore, since the conveying carriage is self-propelled, the guide and conveying tracks may be essentially «passive», and therefore be defined by simple elements, such as guide slides, which considerably simplifies the conveying system according to the present invention and increases the reliability of such a system, reduces the costs thereof and enables more rapid and easy installation.

The conveying system may further present one or more of the following features, considered separately or in combination.

According to an embodiment of the invention, the conveying system is a conveying system for an automatic analysis system for in vitro diagnosis. Advantageously, the conveying system is configured to convey containers supports toward at least one analysis and/or measurement station.

According to an embodiment of the invention, when in the drive position, the drive element is configured to be secured in translation with the containers support received on the support guide element.

According to an embodiment of the invention, the support guide element is configured to receive and guide at least a base of the containers support in translation.

According to an embodiment of the invention, the self-propelled conveying carriage is displaceable along a conveying track in a first direction of displacement and in a second direction of displacement opposite to the first direction of displacement.

According to an embodiment of the invention, the guide track is substantially rectilinear.

According to an embodiment of the invention, the conveying track is substantially parallel to the guide track.

According to an embodiment of the invention, the support guide element is arranged to guide the containers support in translation substantially parallel to an extension direction of the containers support.

According to an embodiment of the invention, the support guide element includes a first lateral guide surface configured to cooperate with a first lateral surface of the containers support, and a second lateral guide surface configured to cooperate with a second lateral surface of the containers support opposite to the first lateral surface.

According to an embodiment of the invention, the self-propelled conveying carriage and the support guide element are arranged to hold the containers support substantially vertical during its displacements along the guide track.

According to an embodiment of the invention, the drive element is pivotally mounted about a pivot axis and between the drive position and the release position.

According to an embodiment of the invention, the drive element includes two drive branches spaced from each other and configured to cooperate with the containers support when the drive element is in its drive position. Advantageously, the two drive branches are spaced from each other by a distance substantially corresponding to the length of the containers support.

According to an embodiment of the invention, the two drive branches are configured to cooperate respectively with opposite lateral walls of the containers support.

According to an embodiment of the invention, each drive branch includes a hooking finger configured to be inserted into a respective hooking notch formed on the containers support.

According to an embodiment of the invention, the pivot axis extends substantially parallel to the conveying track.

According to an embodiment of the invention, the self-propelled conveying carriage includes an actuation device configured to displace the drive element between the drive and release positions. According to an embodiment of the invention, the actuation device is configured to make the drive element pivot about its pivot axis. The actuation device may include different types of actuators, such as a motor rotatably coupled to the drive element.

According to an embodiment of the invention, the self-propelled conveying carriage includes at least one drive wheel, and at least one rotational drive mechanism configured to drive the at least one drive wheel in rotation. For example, the at least one rotational drive mechanism includes a drive motor rotatably coupled to the at least one drive wheel.

According to an embodiment of the invention, the self-propelled conveying carriage includes a carriage body on which the at least one drive wheel is mounted.

According to an embodiment of the invention, the self-propelled conveying carriage includes two drive wheels. For example, the two drive wheels may be motorized independently of each other. To this end, the self-propelled conveying carriage may include two rotational drive mechanisms each configured to drive a respective drive wheel in rotation.

According to an embodiment of the invention, the conveying system includes a carriage guide element defining the conveying track, the carriage guide element being configured to receive and guide the self-propelled conveying carriage during the displacements of the self-propelled conveying carriage along the conveying track.

According to an embodiment of the invention, the support guide element is a support guide slide.

According to an embodiment of the invention, the carriage guide element is a carriage guide slide.

According to an embodiment of the invention, the self-propelled conveying carriage includes guide rollers configured to cooperate with the carriage guide element during the displacements of the self-propelled conveying carriage along the conveying track.

According to an embodiment of the invention, the conveying system comprises at least one sampling or transfer area, also called receiving area, disposed along the guide track and outside the guide track, the self-propelled conveying carriage being configured to displace the containers support received on the support guide element into the at least one sampling or transfer area so as to release the guide track.

According to an embodiment of the invention, the at least one sampling or transfer area is intended to be disposed in the proximity of a samples processing station.

According to an embodiment of the invention, the at least one sampling or transfer area includes a sampling location arranged to receive and store at least temporarily the containers support.

According to an embodiment of the invention, the conveying system includes detection means arranged to detect the reception of a containers support in the at least one sampling or transfer area.

According to an embodiment of the invention, the conveying system includes at least one positioning marking disposed on the conveying track, and the self-propelled conveying carriage includes detection means, such as an optical reader, an RFID or inductive detector, arranged to detect the at least one positioning marking, and control means, such as an integrated circuit or a microprocessor, arranged to control the immobilization of the self-propelled conveying carriage when the detection means detect the at least one positioning marking. For example, the conveying system includes at least one positioning marking disposed opposite the at least one sampling or transfer area.

According to an embodiment of the invention, the at least one positioning marking may be formed by an optical barrier, a barcode, a QR code or still an RFID label disposed on the conveying track.

According to an embodiment of the invention, the support guide element includes a passage opening leading into the at least one sampling or transfer area intended to the passage of a containers support.

According to an embodiment of the invention, the self-propelled conveying carriage includes a carriage body and a support element on which the drive element is movably mounted, the support element being mounted movable in translation relative to the carriage body according to a direction of displacement transverse to the conveying track and between at least one conveying position and one clearance position.

According to an embodiment of the invention, the support element and the drive element are configured such that, when the self-propelled conveying carriage is disposed opposite the at least one sampling or transfer area and the drive element is in the drive position, a displacement of the support element from the conveying position into the clearance position can cause a displacement of the containers support from the guide track into the at least one sampling or transfer area.

According to an embodiment of the invention, the support element includes a pushing surface configured to exert a pushing force against the containers support when the containers support is received on the support guide element and the support element is displaced toward the clearance position. For example, the pushing surface is configured to bear against a lateral surface of the containers support.

According to an embodiment of the invention, the support element and the drive element are configured such that the self-propelled conveying carriage is capable of displacing the containers support from the sampling or transfer area into the guide track.

Advantageously, the support element and the drive element are configured such that, when the self-propelled conveying carriage is disposed opposite the at least one sampling or transfer area and the drive element is in the drive position, a displacement of the support element from the clearance position into the conveying position can cause a displacement of the containers support from the sampling or transfer area into the guide track.

According to an embodiment of the invention, the self-propelled conveying carriage includes a translational drive mechanism configured to displace the support element in translation relative to the carriage body. The translational drive mechanism may include different types of actuators, and may for example include a cylinder comprising a first portion connected to the support element and a second portion connected to the carriage body. According to one variant, the translational drive mechanism may include a rack provided on the support element, and a toothed wheel provided on the carriage body and configured to cooperate with the rack.

According to an embodiment of the invention, the self-propelled conveying carriage includes a battery configured to electrically power the self-propelled conveying carriage. Advantageously, the battery is rechargeable. For example, the battery may be recharged by contact or by induction.

According to an embodiment of the invention, the battery is configured to electrically power the translational drive mechanism, the rotational drive mechanism and/or the actuation device.

According to an embodiment of the invention, the conveying system includes a recharging area including an electric charging device configured to electrically recharge the battery when the self-propelled conveying carriage is located in the recharging area.

According to an embodiment of the invention, the conveying system comprises a loading area intended to store the containers support and comprising a loading device arranged to load the containers support, stored in the loading area, in the guide track defined by the support guide element, and an unloading area in which the containers support is intended to be unloaded.

According to an embodiment of the invention, the conveying system includes a positioning marking disposed opposite the loading area and a positioning marking disposed opposite the unloading area.

According to an embodiment of the invention, the loading device includes a self-propelled loading carriage displaceable along a loading track, the self-propelled loading carriage comprising a drive element movably mounted between a drive position in which the drive element is configured to transmit a drive movement to the at least one containers support stored in the loading area, and a release position in which the drive element is configured to release said containers support, the self-propelled loading carriage being configured to displace said containers support in translation along the loading track and to insert said containers support on the support guide element when the self-propelled loading carriage is displaced along the loading track and when the drive element is in the drive position.

According to an embodiment of the invention, the loading track is transverse to the guide track.

According to an embodiment of the invention, the drive element is mounted movable in translation between the drive position and the release position, for example according to a substantially vertical direction of displacement.

According to an embodiment of the invention, the drive element is configured to grasp or hook the containers support when the drive element is in the drive position.

According to an embodiment of the invention, the self-propelled conveying carriage is configured to displace a containers support, received in the support guide element, into the unloading area.

According to an embodiment of the invention, the loading area includes first guide means arranged to guide a containers support stored in the loading area in translation according to a loading direction. For example, the first guide means may include a guide rail.

According to an embodiment of the invention, the unloading area includes second guide means arranged to guide a containers support unloaded in the unloading area in translation according to an unloading direction. For example, the second guide means may include a guide rail.

According to an embodiment of the invention, the first and/or second guide means are arranged to guide a containers support in translation substantially perpendicular to the extension direction of the containers support.

According to an embodiment of the invention, the first and/or second guide means are configured to cooperate with complementary guide means provided on each containers support, and more particularly on the base of each containers support. For example, the first and/or second guide means are configured to cooperate with a guide notch having a complementary shape provided in the base of each containers support.

According to an embodiment of the invention, the conveying system includes an identification code reading device configured to optically read identification codes borne by containers supported by the containers support when the containers support is received on the support guide element. For example, the information recorded in each identification code may include the reference number of the respective sample, which relates in a univocal manner to the name of the donor of the respective sample.

According to an embodiment of the invention, the identification code reading device is mounted movable in translation according to a direction of displacement substantially parallel to the conveying track.

According to an embodiment of the invention, the identification codes borne by the containers are formed by barcodes, for example one-dimensional or two-dimensional, or QR codes disposed on the external surface of the containers.

According to an embodiment of the invention, the conveying system comprises a rotational drive module configured to drive containers supported by the containers support in rotation when the containers support is received on the support guide element, so as to enable the reading of the identification codes borne by said containers by the identification code reading device.

According to an embodiment of the invention, the rotational drive module includes an actuation member mounted movable in rotation about a vertical axis, and arranged to drive a containers supported by the containers support in rotation about an extension axis of said containers.

According to an embodiment of the invention, the rotational drive module comprises first displacement means arranged to displace the actuation member in translation along a first direction of displacement substantially parallel to the conveying track, and second displacement means arranged to displace the actuation member in translation along a substantially vertical second direction of displacement.

According to an embodiment of the invention, the conveying system includes a control unit configured to remotely communicate with the self-propelled conveying carriage. The control unit may consist of a computer, for example a PC-type computer.

According to an embodiment of the invention, the control unit is configured to wirelessly communicate, for example by WiFi or Bluetooth, with the self-propelled conveying carriage.

According to an embodiment of the invention, the conveying system includes a storage rotor with a substantially vertical axis of rotation, the storage rotor including a plurality of storage housings each configured to receive a containers support coming from the guide track. Such a storage rotor allows temporarily storing containers supports, and enabling their reinsertion into the first or second guide track possibly for conveyance toward an analysis and/or measurement station before unloading them.

According to an embodiment of the invention, the conveying system comprises rotational drive means associated to the storage rotor and arranged to drive the storage rotor in rotation about its axis of rotation.

According to an embodiment of the invention, the rotational drive means associated to the storage rotor are arranged to drive the storage rotor in rotation in a first direction and in a second direction opposite to the first direction.

According to an embodiment of the invention, the storage rotor is disposed at one end of the conveying track.

According to an embodiment of the invention, the conveying system includes first and second support guide elements respectively defining first and second guide tracks, the first and second support guide elements being disposed on either side of the conveying track, the drive element of the self-propelled conveying carriage being movably mounted between a first drive position in which the drive element is configured to transmit a drive movement to a containers support received on the first support guide element, a second drive position in which the drive element is configured to transmit a drive movement to a containers support received on the second support guide element, and a release position in which the drive element is configured to release said containers supports.

Advantageously, the self-propelled conveying carriage is configured to displace the containers support received on the first support guide element in translation along the first guide track when the self-propelled conveying carriage is displaced along the conveying track and when the drive element is in the first drive position, and to displace the containers support received on the second support guide element in translation along the second guide track when the self-propelled conveying carriage is displaced along the conveying carriage and when the drive element is in the second drive position.

Advantageously, the support element is movable between a first clearance position and a second clearance position, the support element and the drive element being configured such that, when the self-propelled conveying carriage is disposed opposite the unloading area and the drive element is in the drive position, a displacement of the support element from the conveying position into the second clearance position causes a displacement of the containers support from the guide track into the unloading area.

According to an embodiment of the invention, the storage rotor is configured to enable a transfer of a sample support from the first support guide element into the second support guide element, and vice versa.

According to an embodiment of the invention, the conveying system includes a transfer device configured to transfer a containers support from the first support guide element into the second support guide element, and vice versa. These arrangements enable an easy and rapid transfer of a containers support between the first and second guide tracks.

According to an embodiment of the invention, the transfer device includes a main conveying portion, first and second transfer portions disposed on either side of the main conveying portion, and first and second secondary conveying portions disposed on either side of the first and second transfer portions, the transfer device being displaceable between a conveying position in which the first and second transfer portions partially define respectively the first and second guide tracks and the main conveying portion partially defines the conveying track, a first transfer position in which the first transfer portion and the first secondary conveying portion partially define respectively the second guide track and the conveying track, and a second transfer position in which the second transfer portion and the second secondary conveying portion partially define respectively the first guide track and the conveying track.

According to an embodiment of the invention, the transfer device is movable in translation according to a direction of displacement extending transverse to the conveying track, and advantageously substantially perpendicular to the conveying track.

According to an embodiment of the invention, the first support guide element includes a loading opening disposed opposite the loading area and intended to the passage of a containers support, and the second support guide element includes an unloading opening disposed opposite the unloading area and intended to the passage of a containers support.

According to an embodiment of the invention, the conveying system includes at least one containers support intended to support containers.

According to an embodiment of the invention, the at least one containers support extends according to an extension direction. Advantageously, the at least one containers support presents a parallelepiped general shape.

According to an embodiment of the invention, the at least one containers support includes a plurality of receiving housings, for example cylindrical, aligned according to the extension direction of the at least one containers support. Advantageously, each receiving housing is open upwards.

According to an embodiment of the invention, the at least one containers support comprises reading apertures enabling an optical reading of the identification codes borne by the containers received on the containers support. Advantageously, each reading aperture opens into a respective receiving housing.

According to an embodiment of the invention, the at least one containers support is configured to support sample tubes.

The present invention further concerns an automatic analysis system for in vitro diagnosis, comprising a conveying system according to the invention, and at least one samples processing station, such as an analysis and/or measurement station, disposed along the guide track.

According to an embodiment of the invention, the at least one samples processing station is disposed in the proximity of the at least one sampling or transfer area.

According to an embodiment of the invention, the at least one samples processing station consists of an analysis and/or measurement station for in vitro diagnosis, and more particularly for carrying out blood tests, such as whole-blood tests.

According to an embodiment of the invention, the at least one samples processing station includes at least one module among a spectrophotometric reading module, a fluorescence reading module, a luminescence reading module, a coagulation measurement module.

According to an embodiment of the invention, the at least one samples processing station includes a support stirring device, and a transfer device configured to transfer a containers support between the sampling or transfer area and the stirring device.

According to an embodiment of the invention, the at least one samples processing station includes an analysis device as described in the document FR2998057.

According to an embodiment of the invention, the at least one samples processing station includes a sampling device configured to collect samples in the containers supported by a containers support, and for example in the containers supported by a containers support received in the at least one sampling or transfer area.

According to an embodiment of the invention, the sampling device includes a sampling head equipped with a sampling needle, first displacement means arranged to displace the sampling head in translation along a direction substantially horizontal and substantially parallel to the guide track, and second displacement means arranged to displace the sampling head along a substantially vertical direction.

According to an embodiment of the invention, the at least one samples processing station includes detection means arranged to detect the reception of a containers support in the at least one sampling or transfer area.

According to an embodiment of the invention, the automatic analysis system includes a plurality of samples processing stations disposed along the guide track.

BRIEF DESCRIPTION OF THE DRAWINGS

Anyway, the invention will be better understood from the following description with reference to the appended schematic drawing representing, as a non-limiting example, an embodiment of this conveying system.

DETAILED DESCRIPTION

Figure 1:
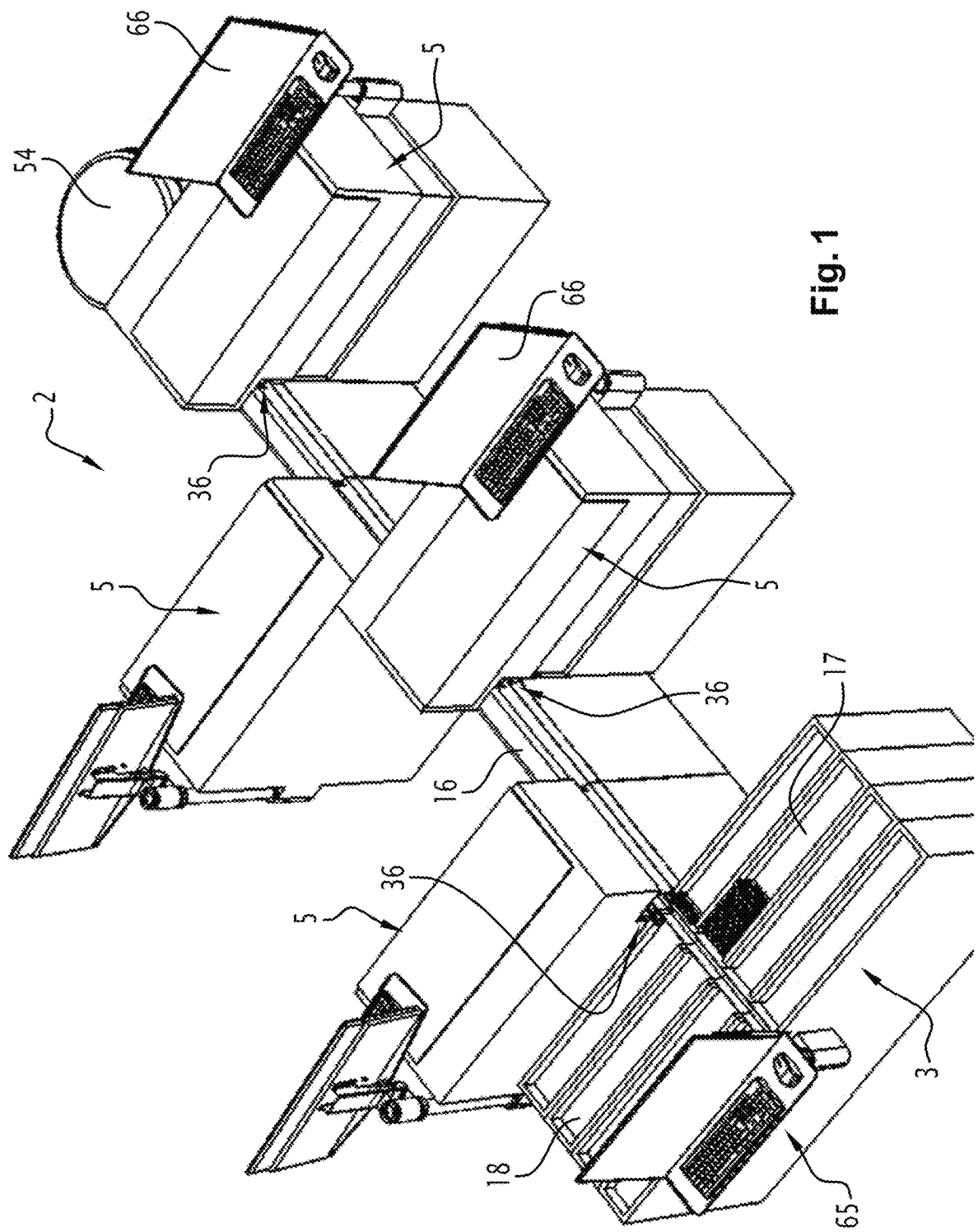
FIG. 1 is a perspective view of an automatic analysis system for in vitro diagnosis according to the invention.

FIG. 1 represents an automatic analysis system 2 for in vitro diagnosis comprising a conveying system 3 configured to convey containers supports 4, and a plurality of analysis and/or measurement stations 5 disposed along the conveying system 3. For example, each analysis and/or measurement station 5 may include one or several module(s) chosen in particular among a spectrophotometric reading module, a fluorescence reading module, a luminescence reading module, and a coagulation measurement module.

Figure 5:
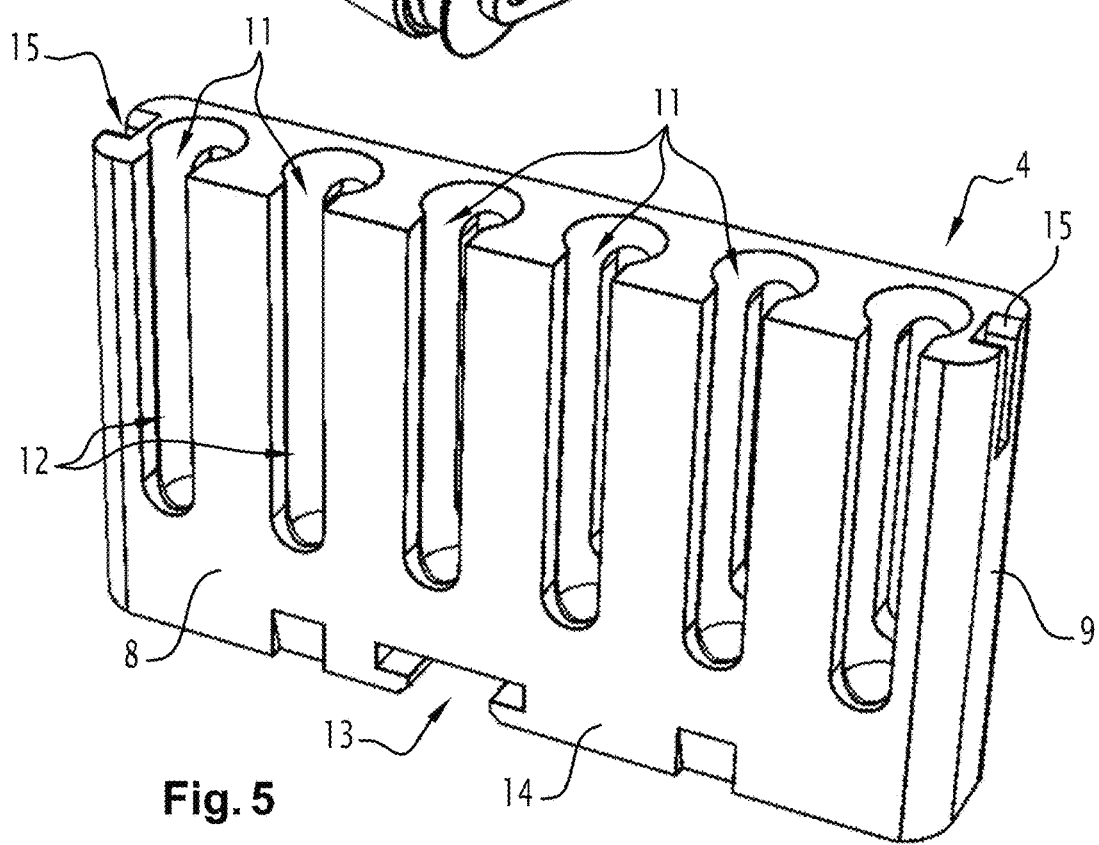
FIG. 5 is a perspective view of the containers support of FIG. 4.
Figure 10:
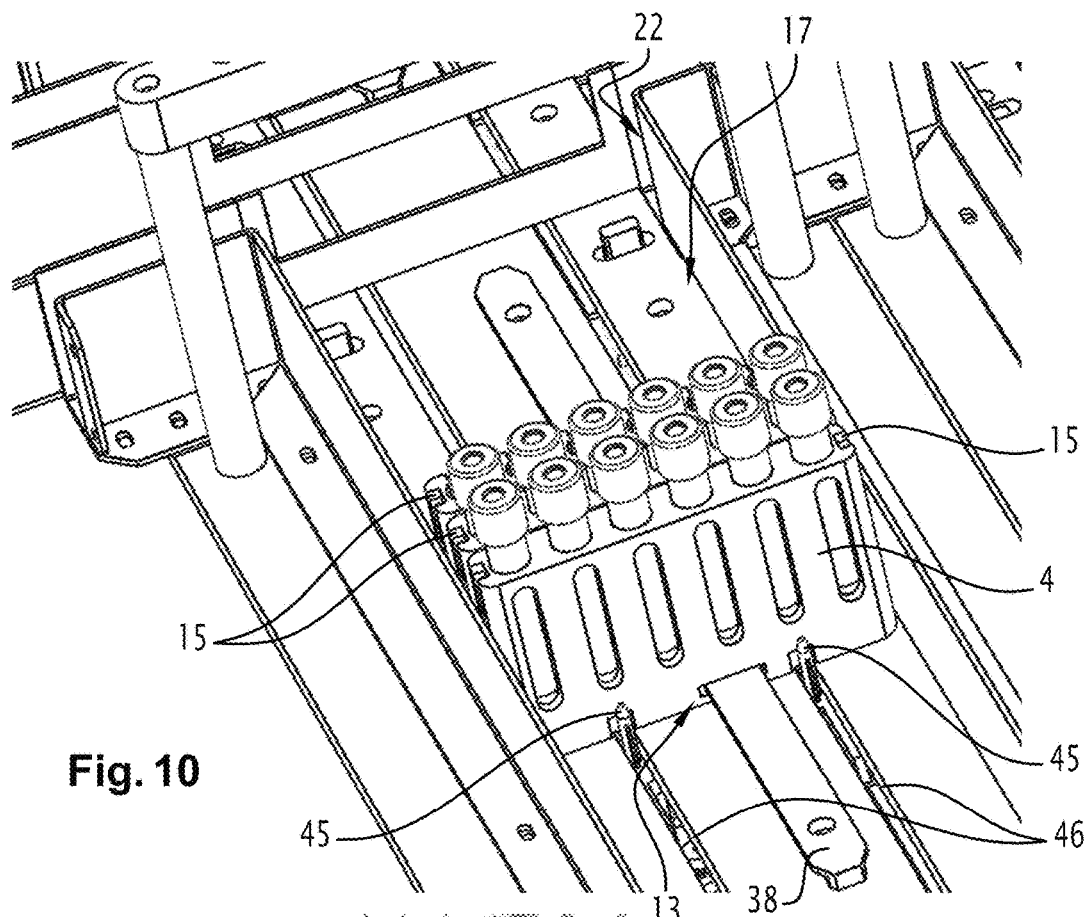
FIG. 10 is a partial perspective view of a loading area belonging to the analysis system.

As shown more particularly in FIGS. 5 and 10, the conveying system 3 comprises a plurality of containers supports 4, also called crates, racks or storages, each intended to support a plurality of containers 6 equipped with plugging elements 7 and containing samples of a biological liquid to analyze, such as blood, plasma or still blood serum samples. Advantageously, the containers 6 consist of sample tubes.

Each containers support 4 presents a parallelepiped general shape, and extends according to an extension direction. More particularly, each containers support 4 includes two longitudinal faces 8 opposite to each other, and two transverse faces 9 opposite to each other.

Each containers support 4 includes a plurality of receiving housings 11, preferably cylindrical, aligned according to the extension direction of said containers support. Advantageously, the receiving housings 11 are open upwards in order to enable easy introduction and removal of the containers 6 into and out of the receiving housings. According to the embodiment represented in the figures, each containers support 4 includes six receiving housings 11, and is therefore configured to receive six containers 6. However, each containers support 4 may include less or more than six receiving housings 11.

Each containers support 4 comprises a plurality of reading apertures 12 enabling an optical reading of identification codes borne by the containers 6 received on said containers support.

In addition, each containers support comprises a guide notch 13 formed on its base 14, and two hooking notches 15 respectively formed on its two transverse faces 9. Each hooking notch 15 is configured to extend substantially vertically under use conditions, and advantageously extends parallel to the extension direction of the respective receiving housings 11.

The conveying system 3 further comprises a conveying unit 16 configured to convey containers supports 4 toward the analysis and/or measurement stations 5, at least one loading area 17 configured to store and load containers supports 4 into the conveying unit 16, and at least one unloading area 18 configured to store and receive containers supports 4 unloaded off the conveying unit 16.

More particularly, the conveying unit 16 comprises first and second support guide elements 19, 21 respectively defining first and second rectilinear and parallel guide tracks. For example, each of the first and second support guide elements 19, 21 is formed by a guide slide. Each of the first and second support guide elements 19, 21 is configured to receive at least the base 14 of a containers support 4. The first support guide element 19 is more particularly configured to guide a containers support 4 in translation along the first guide track, whereas the second support guide element 21 is more particularly configured to guide a containers support 4 in translation along the second guide track.

Figure 13:
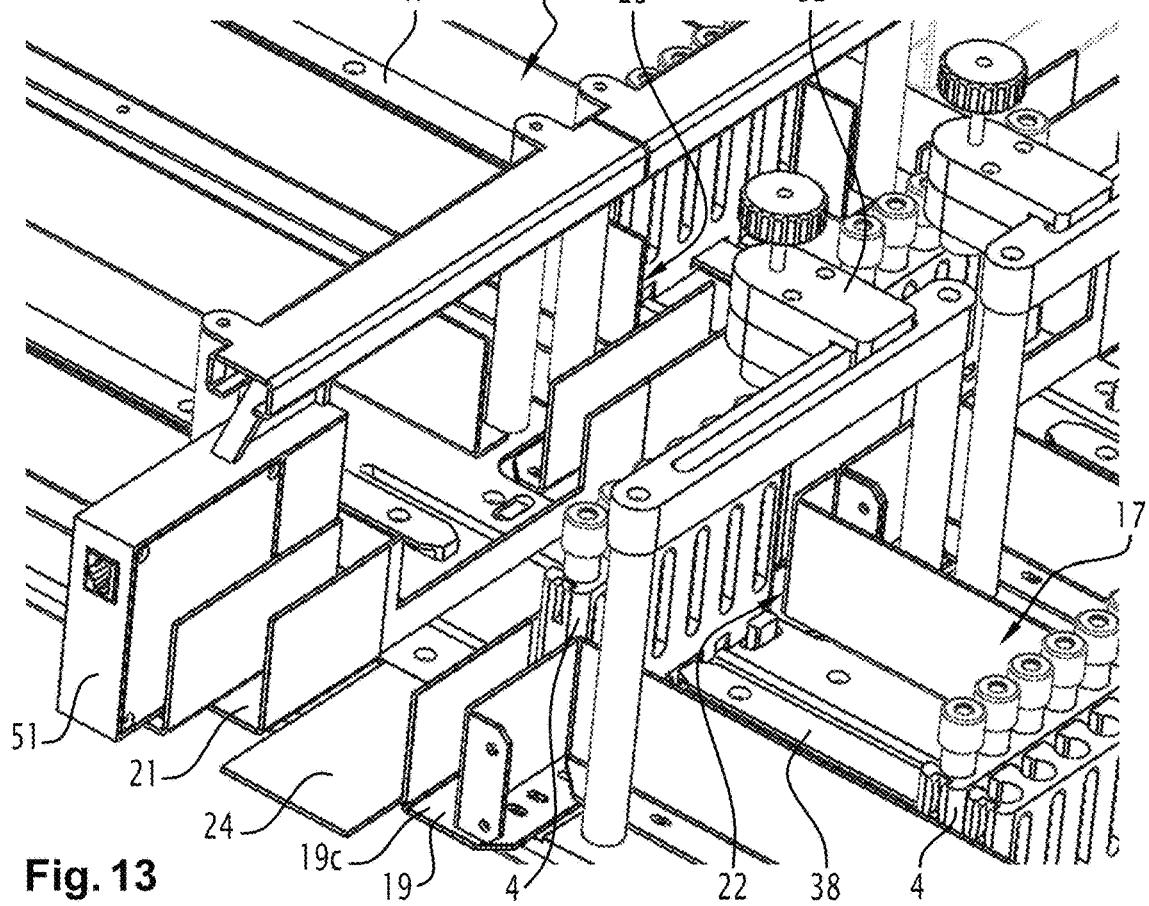
FIG. 13 is a perspective view showing more particularly an identification code reading device belonging to the analysis system.
Figure 14:
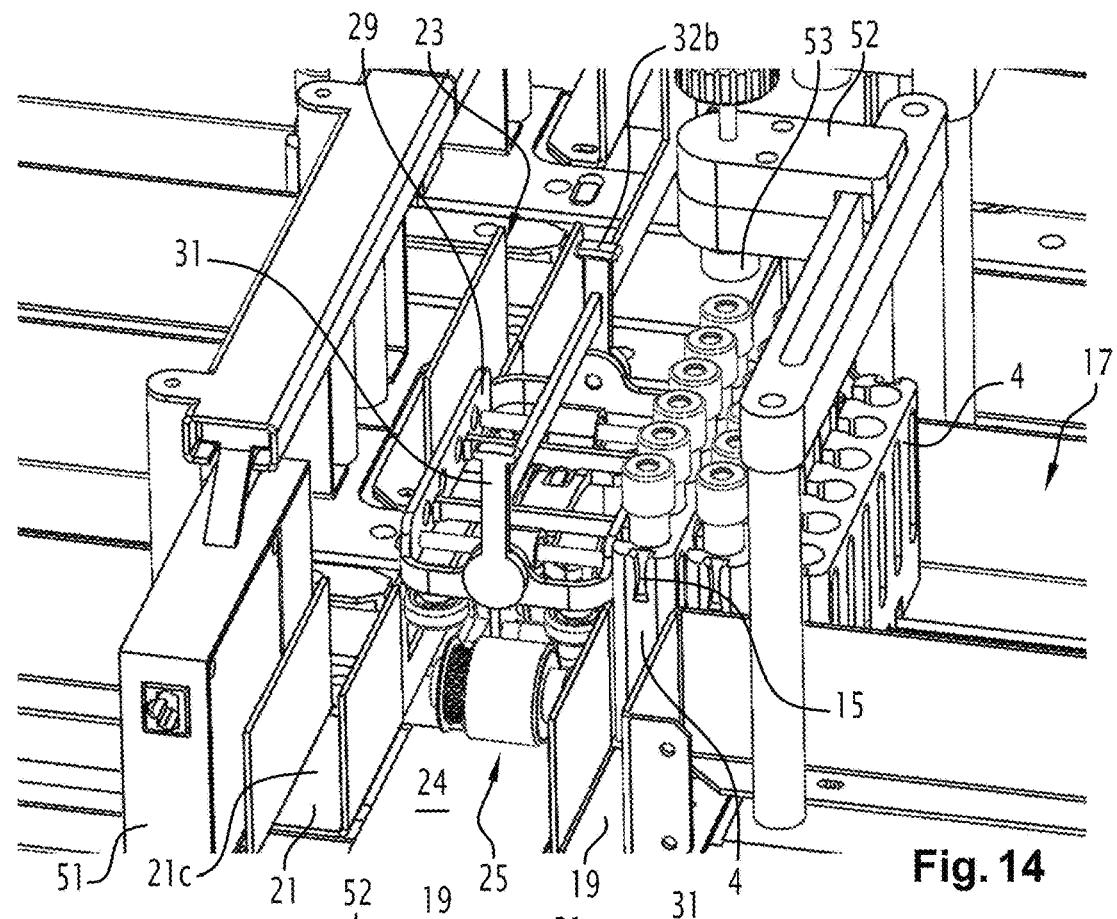
FIG. 14 is a perspective view showing more particularly the conveying carriage opposite the loading area.

As shown more particularly in FIGS. 10 and 13, the first support guide element 19 includes a loading opening 22 disposed opposite the loading area 17 and intended to the passage of a containers support 4, and, as shown more particularly in FIGS. 13 and 14, the second support guide element 21 includes an unloading opening 23 disposed opposite the unloading area 18 and intended to the passage of a containers support 4.

Advantageously, each of the first and second support guide elements 19, 21 presents a width corresponding substantially to the width of the containers supports 4. Thus, each of the first and second support guide elements 19, 21 includes a first lateral guide surface 19a, 21a configured to cooperate with a first longitudinal face 8 of a containers support 4, and a second lateral guide surface 19b, 21b configured to cooperate with a second longitudinal face 8 of a containers support 4 (see in particular FIGS. 7 and 18).

Each of the first and second support guide elements 19, 21 also includes a bottom surface 19c, 21c arranged to cooperate with the lower surface of the base 14 of a containers support 4 during the displacements of the latter along the respective guide track.

The conveying unit 16 also comprises a carriage guide element 24 disposed between the first and second support guide elements 19, 21, and defining a conveying track which is rectilinear and parallel to the first and second guide tracks. For example, the carriage guide element 24 is formed by a guide slide. The carriage guide element 24 includes two lateral guide surfaces 24a, 24b opposite to each other, and a bottom surface 24c (see in particular FIGS. 7 and 18).

In addition, the conveying unit 16 comprises a self-propelled conveying carriage 25 displaceable along the conveying track. As shown more particularly in FIGS. 2 and 3, the self-propelled conveying carriage 25 includes a carriage body 26, and two drive wheels 27 rotatably mounted on the carriage body 26 and intended to roll on the bottom surface 24c of the carriage guide element. Each drive wheel 27 presents an axis of rotation extending perpendicular to the first and second guide tracks.

The self-propelled conveying carriage 25 includes a rotational drive mechanism 28 configured to drive the two drive wheels 27 in rotation. For example, the rotational drive mechanism 28 comprises a drive motor 28a rotatably coupled to the drive wheels 27 via a drive belt 28b.

Each drive wheel 27 can be driven in rotation in a first rotational direction and in a second rotational direction opposite to the first rotational direction. Thus, the self-propelled conveying carriage 25 is displaceable along the conveying track in a first direction of displacement and in a second direction of displacement opposite to the first direction of displacement.

The self-propelled conveying carriage 25 further includes a support element 29, for example in the form of a support frame extending horizontally, mounted movable in translation relative to the carriage body 26 according to a direction of displacement horizontal and perpendicular to the conveying track. Advantageously, the direction of displacement of the support element 29 is perpendicular to the extension direction of the carriage body 26.

Figure 6:
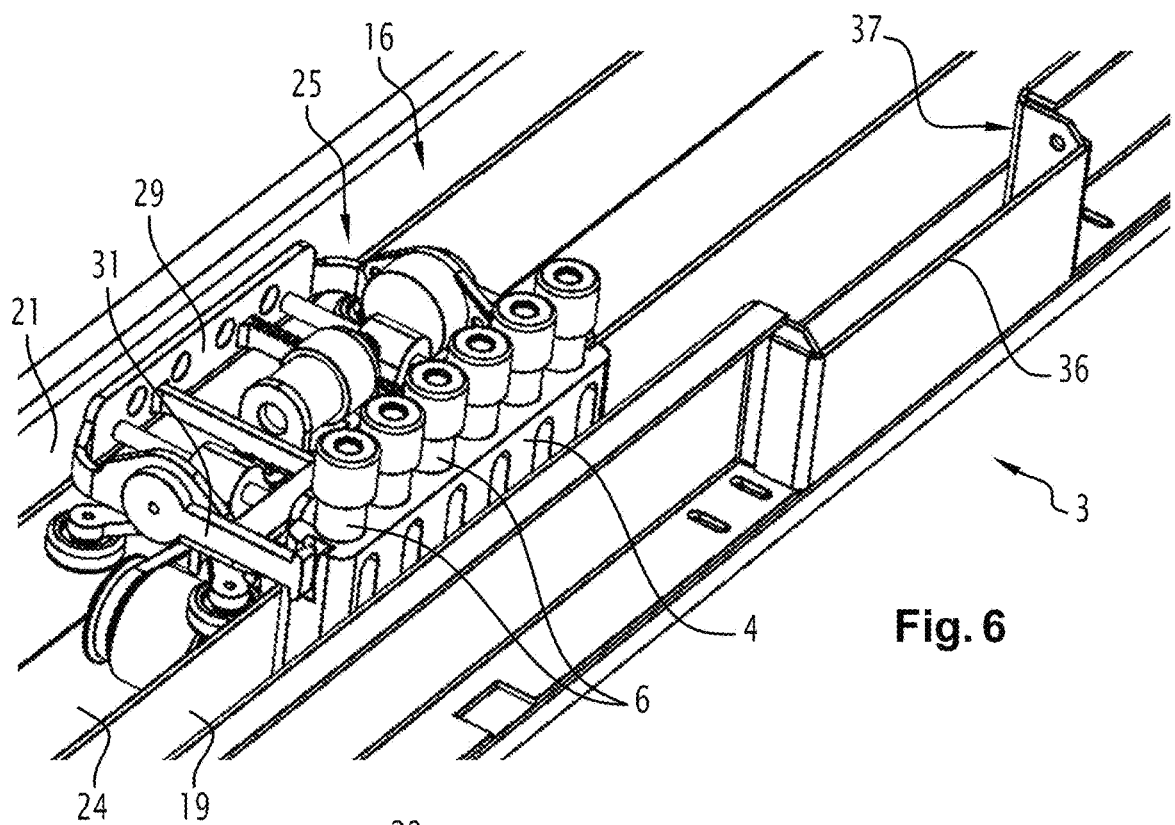
FIGS. 6 to 9 are partial perspective views of the analysis system showing the conveying carriage in different operating positions.

More particularly, the support element 29 can occupy a conveying position (see FIG. 6) in which the support element 29 extends integrally or substantially integrally above the conveying track, a first clearance position (see FIG. 8) in which the support element 29 extends partially above the first guide track, and a second clearance position in which the support element 29 extends partially above the second guide track.

The support element 29 further comprises a first pushing surface 29a configured to exert a pushing force against a containers support 4 received in the first support guide element 19 when the support element 29 is displaced into the first clearance position, and a second pushing surface 29b, opposite to the first pushing surface 29a, configured to exert a pushing force against a containers support 4 received in the second support guide element 21 when the support element 29 is displaced into the second clearance position. More particularly, each of the first and second pushing surfaces 29a, 29b is configured to bear against a longitudinal face 8 of a containers support 4.

The self-propelled conveying carriage 25 also includes a translational drive mechanism 30 configured to displace the support element 29 in translation relative to the carriage body 26, and more particularly to displace the support element 29 between the conveying position and the first and second clearance positions. For example, the translational drive mechanism 30 may include a rack 30.1 provided on the support element 29 and a drive motor 30.2 provided on the carriage body 26 and secured in rotation to a toothed wheel 30.3 configured to cooperate with the rack 30.1. The translational drive mechanism 30 may include other types of actuators known to those skilled in the art, such as a cylinder comprising a first portion connected to the support element 29 and a second portion connected to the carriage body 26.

It should be noted that the self-propelled conveying carriage 25 and the first and second support guide elements 19, 21 are arranged to hold the containers supports 4 substantially vertical during their displacements along the respective guide track.

Figure 2:
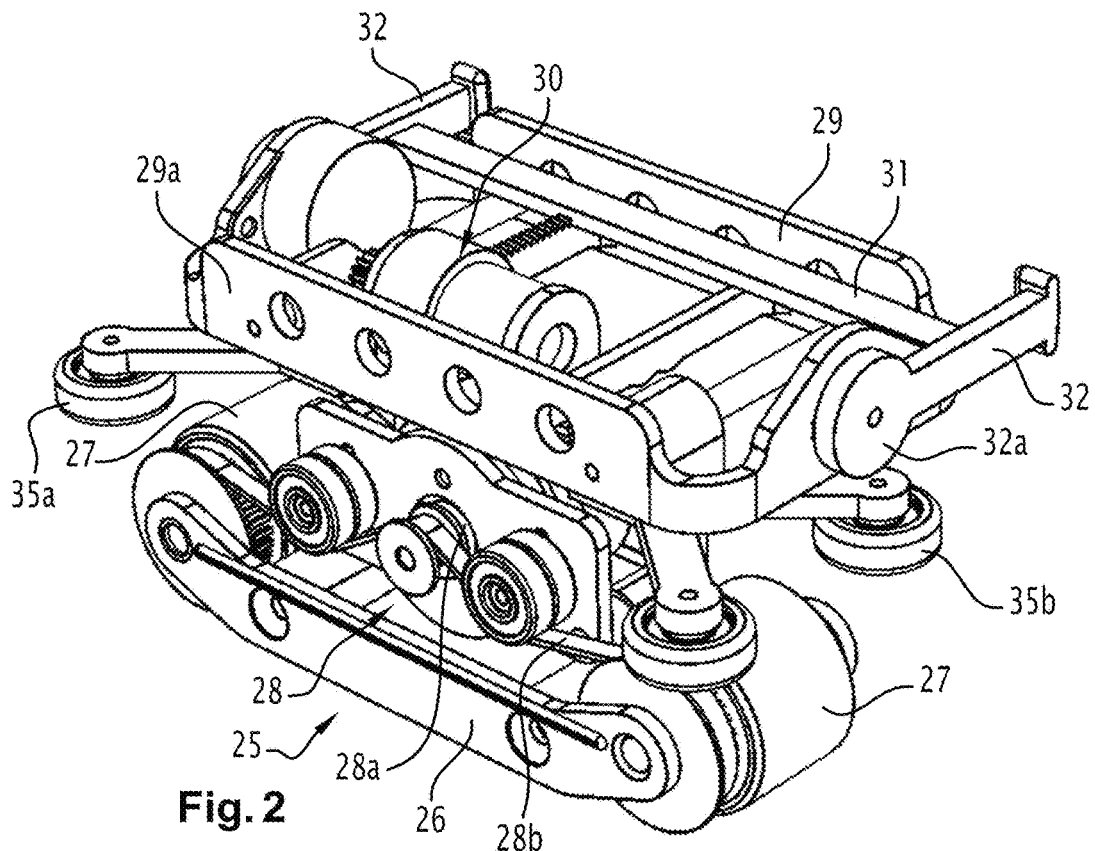
FIGS. 2 and 3 are perspective views of a conveying carriage belonging to the analysis system.
Figure 3:
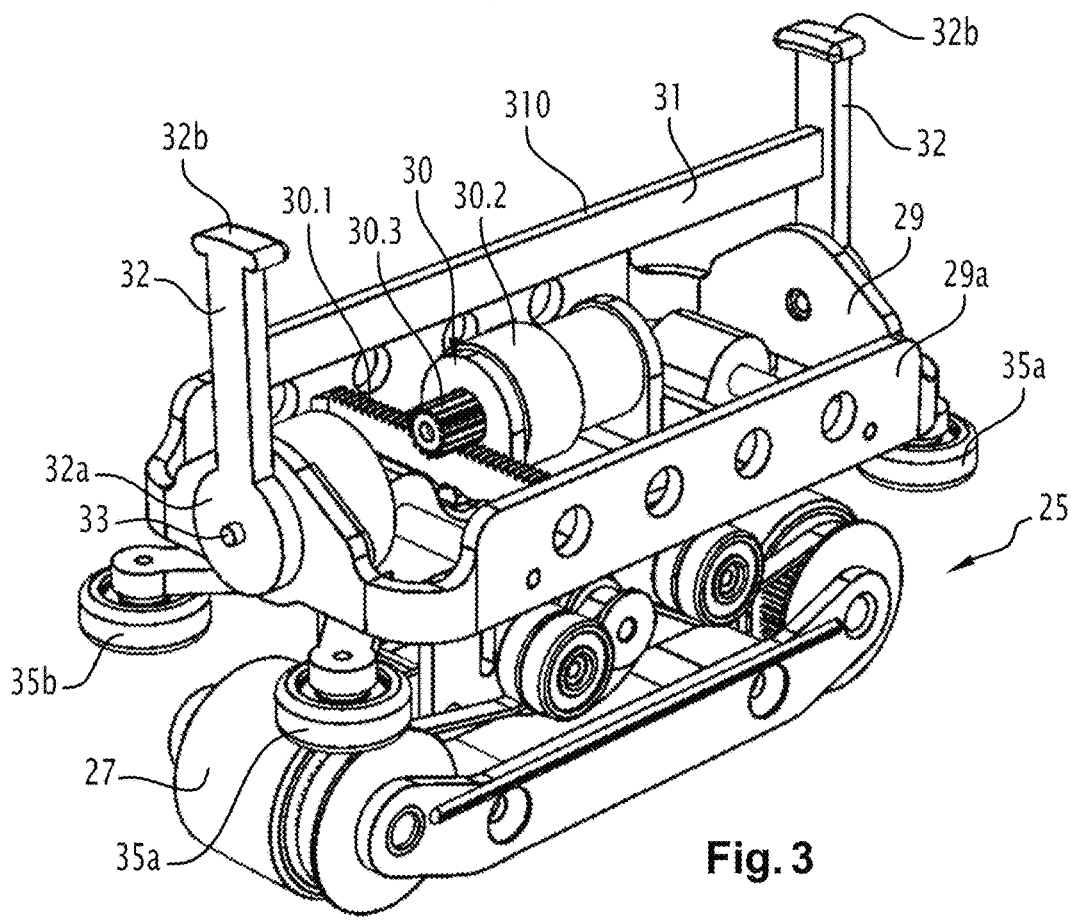

As shown more particularly in FIGS. 2 and 3, the self-propelled conveying carriage 25 includes in addition a drive element 31, for example in the form of a drive yoke, pivotally mounted on the support element 29 about a pivot axis extending substantially parallel to the conveying track and to the extension direction of the carriage body 26. More particularly, the drive element 31 comprises two drive branches 32 spaced from each other by a distance corresponding substantially to the length of the containers supports 4.

Each drive branch 32 includes a mounting portion 32a pivotally mounted on the support element 29, and a hooking finger 32b configured to be inserted into a respective hooking notch 15 formed on a transverse face 9 of a containers support 4. Advantageously, the drive element 31 includes a connecting portion 310 linking the two hooking branches and extending parallel to the pivot axis of the drive element 31.

Figure 4:
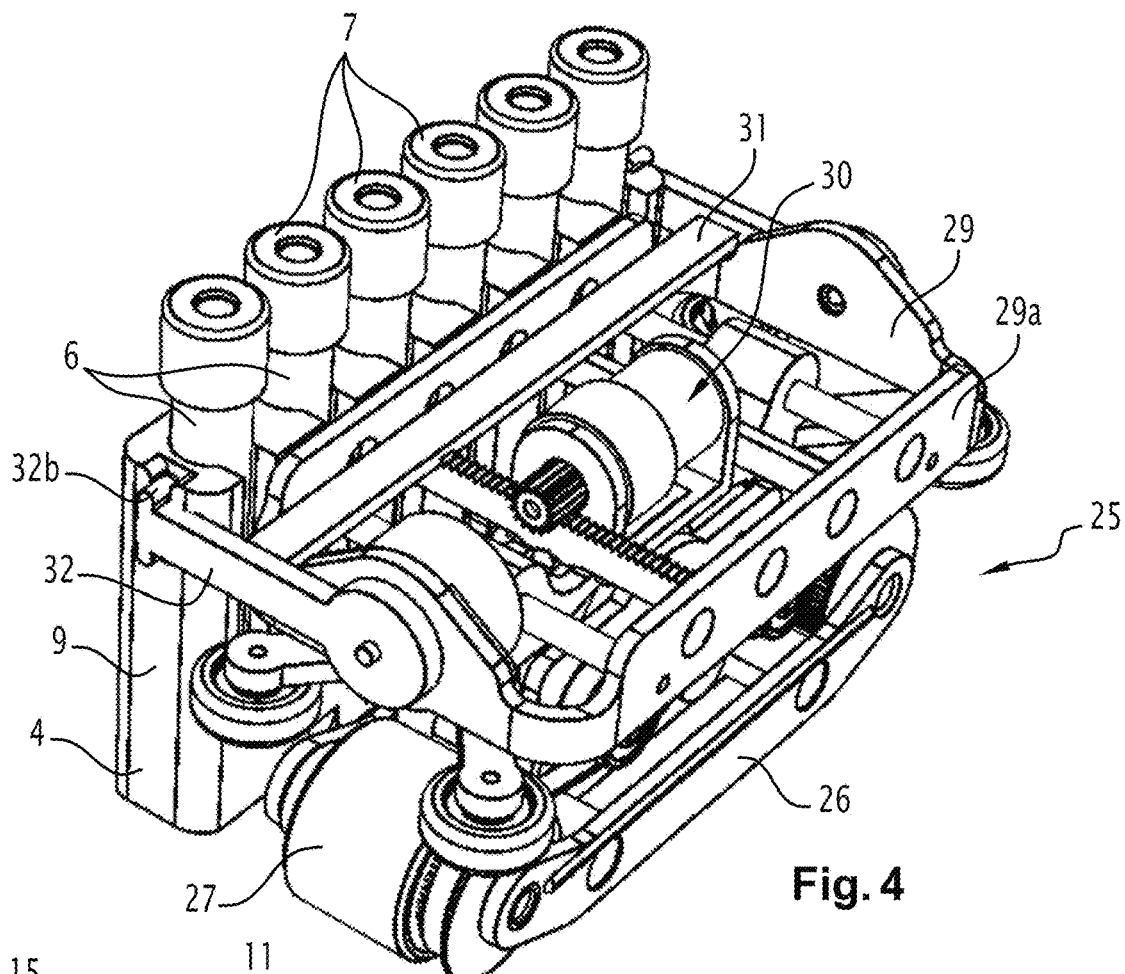
FIG. 4 is a perspective view of a containers support belonging to the analysis system and retained by the conveying carriage of FIG. 2.

More particularly, the drive element 31 can occupy a first drive position (see FIG. 4) in which the hooking fingers 32b can be inserted into the hooking notches 15 formed on a containers support 4 received in the first support guide element 19 and the drive element 31 can transmit a drive movement to the containers support 4 received in the first support guide element 19, a second drive position (see FIG. 15) in which the hooking fingers 32b can be inserted into the hooking notches 15 formed on a containers support 4 received in the second support guide element 21 and the drive element 31 can transmit a drive movement to the containers support 4 received in the second support guide element 21, and a release position (see FIGS. 3 and 14) in which the drive element 31 can release said containers supports 4. Advantageously, the drive element 31 extends substantially horizontally when it lies in the first and second drive positions. For example, the drive element 31 may extend substantially vertically when it lies in the release position.

Thus, the self-propelled conveying carriage 25 is more particularly configured to displace a containers support 4 received in the first support guide element 19 in translation along the first guide track when the self-propelled conveying carriage 25 is displaced along the conveying track and when the drive element 31 is in the first drive position, and to displace a containers support 4 received in the second support guide element 21 in translation along the second guide track when the self-propelled conveying carriage 25 is displaced along the conveying track and when the drive element 31 is in the second drive position.

The self-propelled conveying carriage 25 includes an actuation device 33 configured to make the drive element 31 pivot about its pivot axis and between the first and second drive positions and the release position. The actuation device 33 may include different types of actuators, such as a motor rotatably coupled to the drive element 31.

The self-propelled conveying carriage 25 also includes a battery (not shown in the figures) configured to electrically power the self-propelled conveying carriage, and more particularly the translational drive mechanism 30, the rotational drive mechanism 28 and the actuation device. According to the embodiment represented in the figures, the battery is rechargeable, and may be recharged for example by contact or by induction. To this end, the conveying system 3 includes a recharging area (not shown in the figures) including an electric charging device configured to electrically recharge the battery when the self-propelled conveying carriage 25 is located in the recharging area.

According to the embodiment represented in the figures, the self-propelled conveying carriage 25 further includes a first pair of guide rollers 35a configured to cooperate with the first guide surface 24a, and a second pair of guide rollers 35b configured to cooperate with the second guide surface 24b. Advantageously, each guide roller 35a, 35b presents a substantially vertical axis of rotation.

The conveying system 3 also comprises a plurality of sampling areas 36 disposed along the conveying unit 16. According to the embodiment represented in the figures, the conveying system 3 includes a plurality of sampling areas 36, two in the case represented in the figures, disposed along the first guide track and outside the first guide track, and a plurality of sampling areas 36, two in the case represented in the figures, disposed along the second guide track and outside the second guide track.

Each sampling area 36 includes a sampling location disposed in the proximity of a respective analysis and/or measurement station 5, and arranged to receive and store at least temporarily a containers support 4. Thus, each of the first and second support guide elements 19, 21 includes a plurality of passage openings 37 each leading into the respective sampling area 36, and each intended to the passage of a containers support 4 from the respective guide track.

Figure 7:
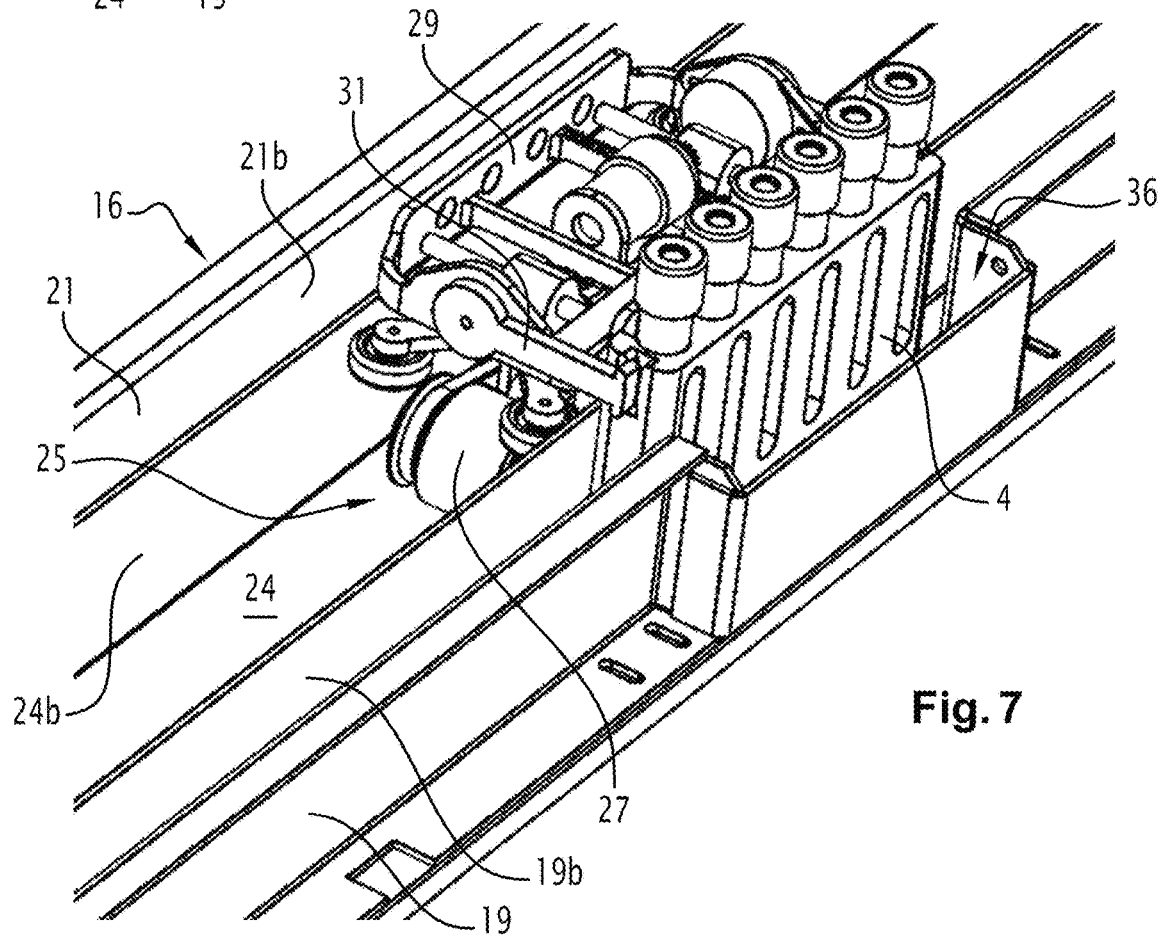
Figure 8:
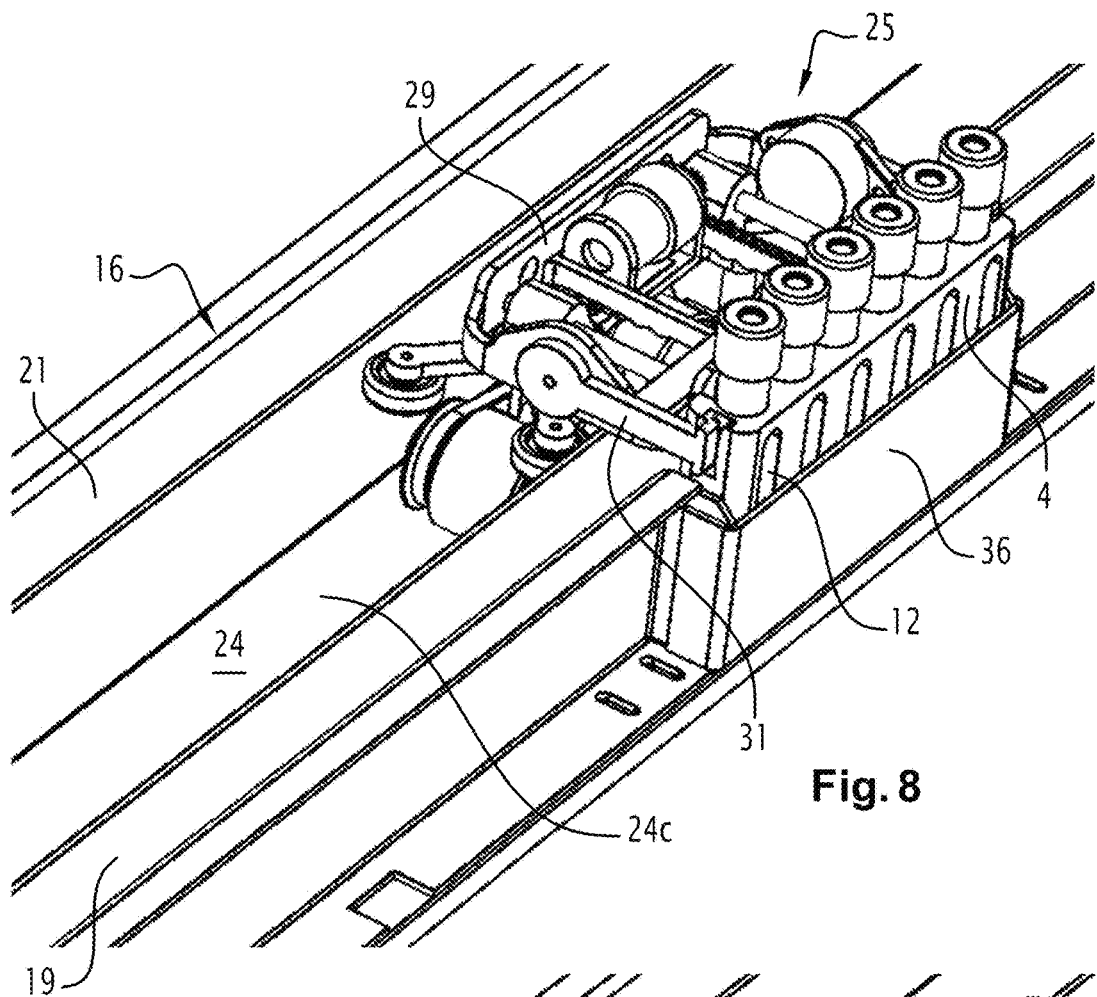

As shown more particularly in FIGS. 7 and 8, the support element 29 and the drive element 31 of the self-propelled conveying carriage 25 are configured such that, when the self-propelled conveying carriage 25 is disposed opposite a sampling area 36 disposed along the first guide track and the drive element 31 is in the first drive position and is coupled to a containers support 4 received in the first guide track, a displacement of the support element 29 from the conveying position into the first clearance position causes a displacement of the containers support 4 into said sampling area 36 so as to release the first guide track. In such a position of the support element 29, the drive element 31 can of course be displaced into the release position in order to release the containers support 4 received in the sampling area 36, and the conveying carriage 25 can then be displaced along the conveying track for example in order to grasp another containers support 4.

The support element 29 and the drive element 31 of the self-propelled conveying carriage 25 are also configured such that, when the self-propelled conveying carriage 25 is disposed opposite a sampling area 36 disposed along the first guide track and receiving a containers support 4, the drive element 31 can first grasp said containers support 4 through successive displacements of the support element 29 into the first clearance position and of the drive element 31 into the first drive position, and then displace the grasped containers support 4 in the first guide track through a displacement of the support element 29 into the conveying position.

Similarly, the support element 29 and the drive element 31 of the self-propelled conveying carriage 25 are also configured to displace a containers support 4 received in the second guide track toward a sampling area 36 disposed along the second guide track, and to displace a containers support 4 received in a sampling area 36 disposed along the second guide track toward the second guide track.

Advantageously, each analysis and/or measurement station 5 includes a sampling device (not represented in the figures) disposed adjacent to the respective sampling area 36, and configured to collect samples in the containers 6 supported by a containers support 4 received in the respective sampling area 36. Advantageously, each sampling device includes a sampling head equipped with a sampling needle, first displacement means arranged to displace the respective sampling head in translation along a direction substantially horizontal and substantially parallel to the conveying track, and second displacement means arranged to displace the respective sampling head in translation along a substantially vertical direction.

Advantageously, each analysis and/or measurement station 5 also includes detection means arranged to detect the reception of a containers support 4 in the respective sampling area 36.

As shown more particularly in FIG. 10, the loading area 17 includes a guide rail 38 extending perpendicular to the conveying track. The guide rail 38 is configured to cooperate with the guide notch 13 of each containers support 4 stored in the loading area 17. More specifically, the guide rail 38 is arranged to guide each containers support 4 stored in the loading area 17 in translation according to a loading direction during their displacements into the loading area 17 and their loading in the conveying unit 16, and more particularly in the first support guide element 19. Advantageously, the loading direction extends substantially perpendicular to the extension direction of each containers support 4 stored in the loading area.

Figure 11:
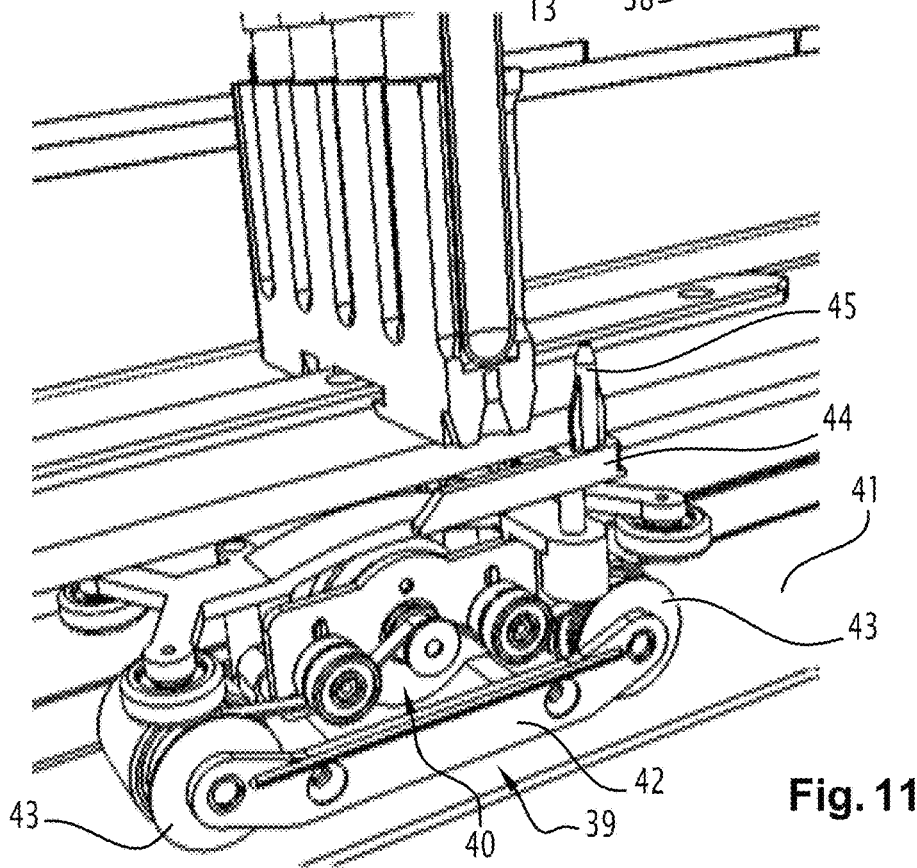
FIG. 11 is a perspective view showing more particularly a loading carriage belonging to the loading area.

The loading area 17 also includes a loading device (see in particular FIG. 11) arranged on the one hand to displace the containers supports 4 stored in the loading area 17 toward the conveying unit 16 and according to the loading direction, and on the other hand to load each containers support 4, stored in the loading area, in the first guide track defined by the first support guide element 19.

According to the embodiment represented in the figures, the loading device includes a self-propelled loading carriage 39 displaceable along a loading track defined by a carriage guide element 41, for example in the form of a guide slide, disposed beneath the guide rail 38. The self-propelled loading carriage 39 includes a carriage body 42, and two drive wheels 43 rotatably mounted on the carriage body 42 and intended to roll on the bottom surface of the carriage guide element 41. Each drive wheel 43 presents an axis of rotation extending parallel to the first and second guide tracks. The self-propelled loading carriage 39 includes a rotational drive mechanism 40 configured to drive the two drive wheels 43 in rotation. For example, the rotational drive mechanism 40 comprises a drive motor rotatably coupled to the drive wheels 43 via a drive belt.

Each drive wheel 43 can be driven in rotation in a first rotational direction and in a second rotational direction opposite to the first rotational direction. Thus, the self-propelled loading carriage 39 is displaceable along the loading track in a first direction of displacement and in a second direction of displacement opposite to the first direction of displacement.

In addition, the self-propelled loading carriage 39 includes a drive element 44, for example in the form of a drive yoke, mounted movable in translation relative to the carriage body 42 according to a substantially vertical direction of displacement. More particularly, the drive element 44 comprises two drive branches 45 (see FIGS. 10 and 11) intended to extend through two parallel slots 46 extending on either side of the guide rail 38 and to cooperate with the base 14 of a containers support 4 stored in the loading area 17.

More particularly, the drive element 44 is mounted movable in translation between a drive position in which the two drive branches 45 protrude from the slots 46 and are configured to cooperate with the base 14 of a containers support 4 stored in the loading area 17 and the drive element 44 is configured to transmit a drive movement to said containers support 4, and a release position in which the two drive branches 45 are disposed set back from the slots 46 or at least below the lower surface of said containers support 4.

Thus, the self-propelled loading carriage 39 is configured to displace each containers support 4 in translation along the loading track, and to successively load each containers support 4 in the first guide track when the self-propelled loading carriage 39 is displaced along the loading track and when the drive element 44 is in the drive position.

Figure 15:
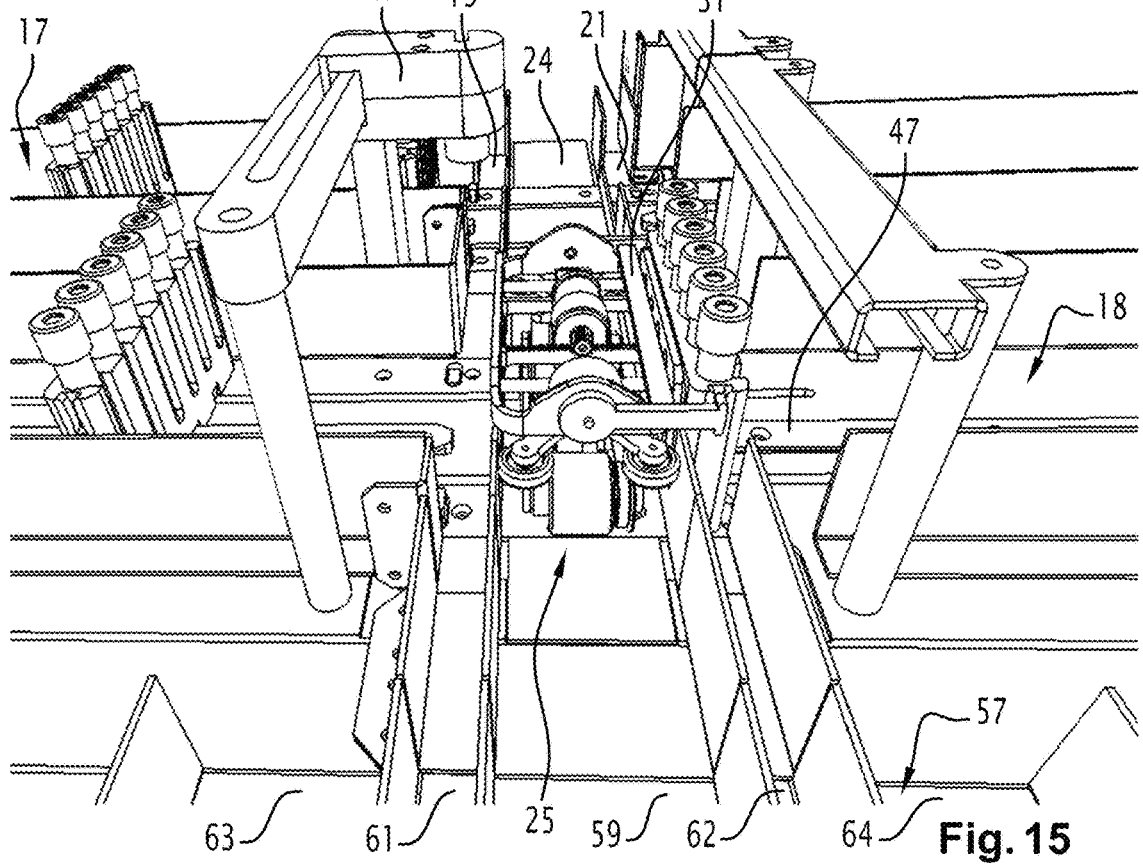
FIGS. 15 and 16 are perspective views showing more particularly the conveying carriage opposite an unloading area belonging to the analysis system.
Figure 16:
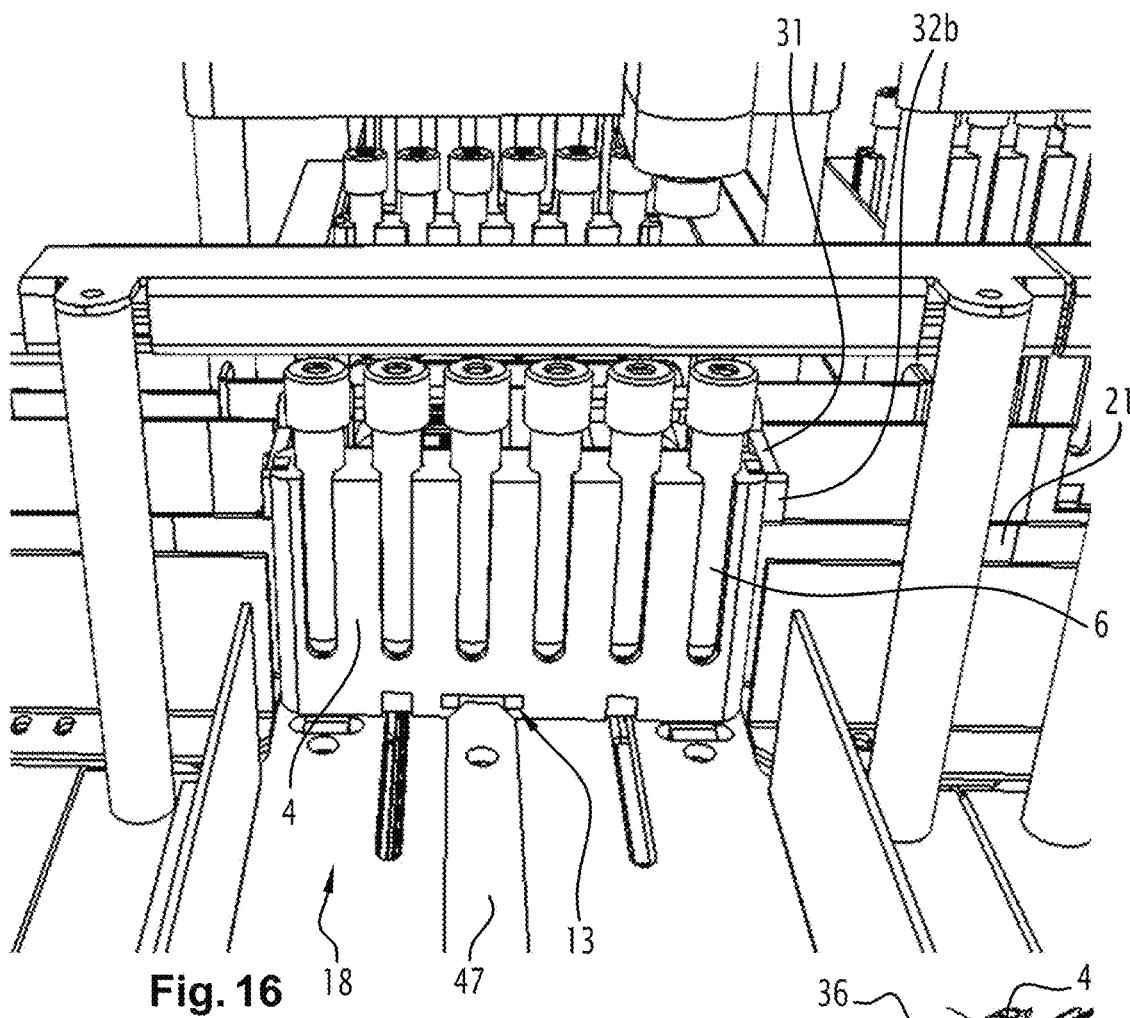

As shown more particularly in FIGS. 15 and 16, the unloading area 18 includes a guide rail 47 extending perpendicular to the conveying track. The guide rail 47 is arranged to guide each containers support 4 unloaded in the unloading area 18 in translation from the second guide track according to an unloading direction. More particularly, the guide rail 47 is configured to cooperate with the guide notch 13 of each containers support 4 unloaded in the unloading area 18. Advantageously, the unloading direction extends substantially perpendicular to the extension direction of each containers support 4 unloaded in the unloading area 18.

According to the embodiment represented in the figures, the self-propelled conveying carriage 25 is configured to displace a containers support 4, disposed in the second support track, into the unloading area 18. In particular, the support element 29 and the drive element 31 are configured such that, when the self-propelled conveying carriage 25 is disposed opposite the unloading area 18 and the drive element 31 is in the drive position and is coupled to a containers support 4 received in the second guide track, a displacement of the support element 29 from the conveying position into the second clearance position causes a displacement of the containers support 4 into the unloading area 18.

Advantageously, the conveying system 3 includes a plurality of positioning markings (not shown in the figures) disposed on the conveying track. For example, the conveying system 3 includes a positioning marking opposite each sampling area 36, a positioning marking opposite the loading area 17 and a positioning marking opposite the unloading area 18. According to such an embodiment of the invention, the self-propelled conveying carriage 25 includes on the one hand detection means, such as an optical reader, an RFID detector or an inductive detector, arranged to detect the positioning markings disposed on the conveying track during the displacements of the self-propelled conveying carriage 25 along the conveying track, and on the other hand control means, such as an integrated circuit or a microprocessor, arranged to control the immobilization of the self-propelled conveying carriage 25 when the detection means detect the positioning marking associated to the area of the conveying system 3 that the self-propelled conveying carriage 25 should reach. For example, each positioning marking may be formed by an optical barrier, a barcode, a QR code or still an RFID label.

Figure 12:
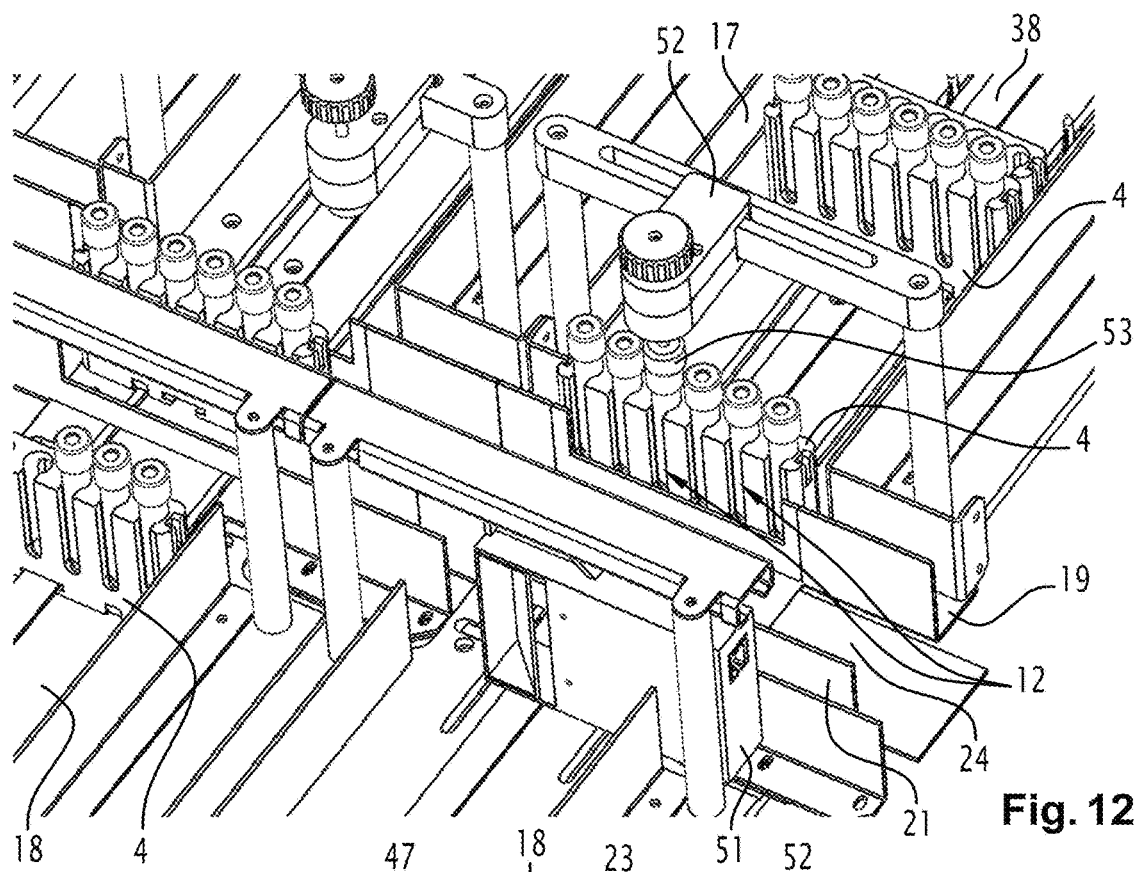
FIG. 12 is a perspective view showing more particularly a rotational drive module belonging to the analysis system.

As shown in FIGS. 12 and 13, the conveying system 3 also includes an identification code reading device 51 configured to optically read identification codes borne by the containers 6 supported by a containers support 4 disposed in the first guide track and opposite the loading area 17. For example, the information recorded in each identification code may consist of the reference number of the respective sample. Advantageously, the identification codes borne by the containers 6 are formed by barcodes or QR codes disposed on the external surface of the containers. Advantageously, the identification code reading device 51 is mounted movable in translation according to a direction of displacement substantially parallel to the conveying track in order to be able to easily optically read the identification codes borne by the different containers 6 of the same containers support 4.

It should be noted that the different conveying destinations of a containers support 4 are advantageously determined according to the identification codes borne by the different containers 4 carried by said containers support 4.

As shown in FIGS. 12 to 14, the conveying system 3 further includes a rotational drive module 52 configured to drive in rotation containers 6 supported by a containers support 4 disposed in the first guide track and opposite the loading area 17, so as to enable the optical reading of the identification codes borne by said containers 6 by the identification code reading device 51 through the respective reading apertures 12. Advantageously, the rotational drive module 52 includes an actuation member 53 mounted movable in rotation about a vertical axis, and arranged to drive a container 6 in rotation about its extension axis. According to the embodiment represented in the figures, the rotational drive module 53 comprises first displacement means arranged to displace the actuation member 53 in translation along a first direction of displacement substantially horizontal and parallel to the conveying track, and second displacement means arranged to displace the actuation member 53 in translation along a substantially vertical direction of displacement.

Figure 17:
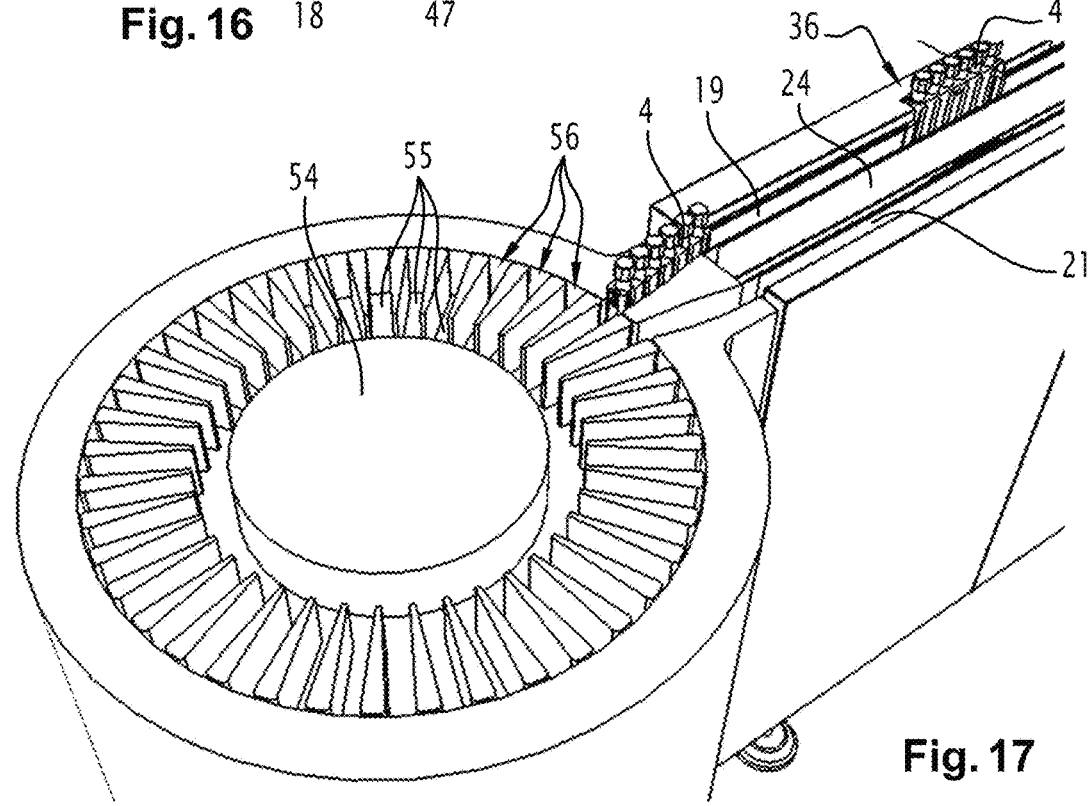
FIG. 17 a perspective view of a storage rotor belonging to the analysis system.

As shown in FIGS. 1 and 17, the conveying system 3 also includes a storage rotor 54, with a substantially vertical axis of rotation, disposed at one end of the conveying track. The storage rotor 54 includes a plurality of storage housings 55 angularly shifted and each configured to store a containers support 4 coming from the first and second guide tracks. Each storage housing 55 extends radially, and more particularly includes a radial introduction opening 56 able to be disposed opposite the first and second guide tracks depending on the angular position of the storage rotor 54.

Advantageously, the conveying system 3 includes rotational drive means associated to the storage rotor 54, and arranged to drive the storage rotor 54 in rotation about its axis of rotation in a first direction and in a second direction opposite to the first direction. Thus, the storage rotor 54 is also configured to transfer a sample support 4 from the first guide track into the second guide track, and vice versa.

Figure 18:
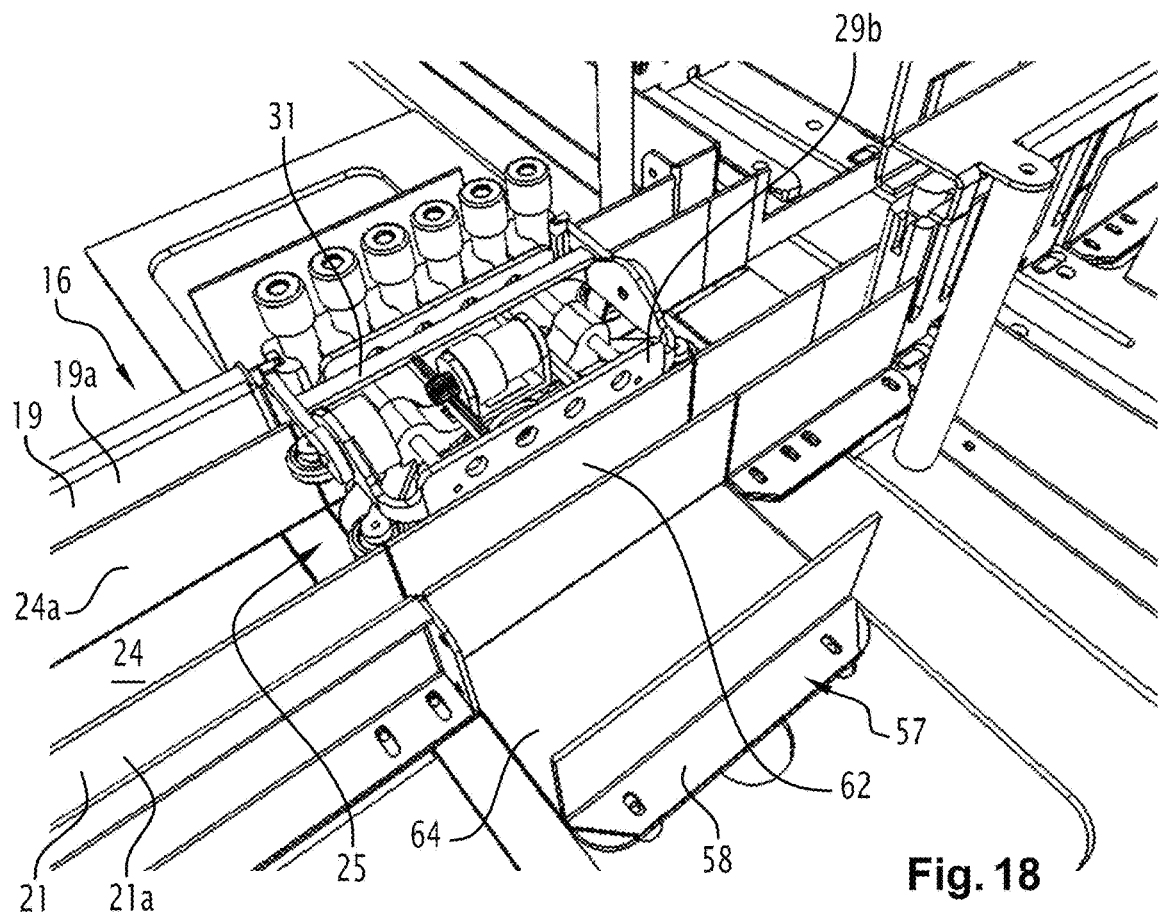
FIGS. 18 and 19 are perspective views showing more particularly a transfer device belonging to the analysis system.
Figure 19:
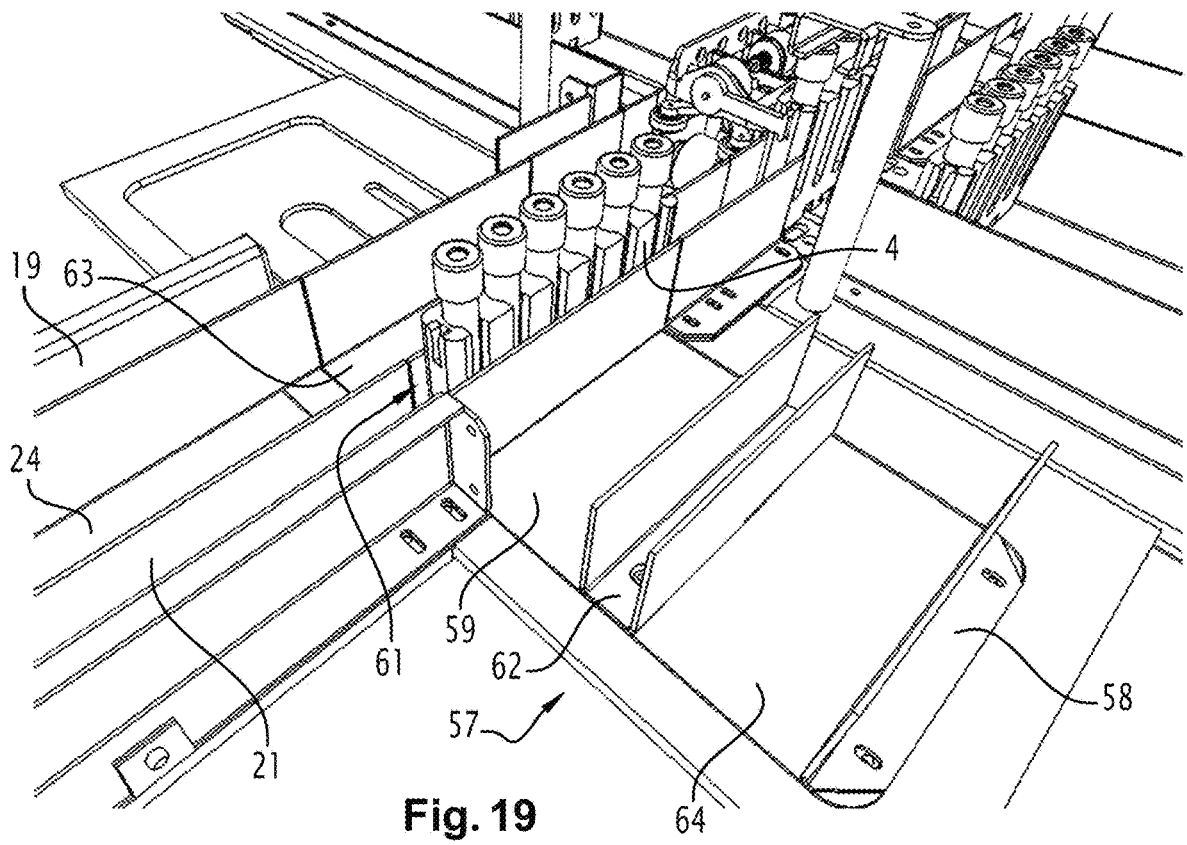

As shown more particularly in FIGS. 15, 18 and 19, the conveying system 3 includes a transfer device 57 disposed along the conveying unit 16 and movable in translation according to a direction of displacement perpendicular to the conveying track. The transfer device 57 is configured to transfer a containers support from the first guide track into the second guide track, and vice versa.

More particularly, the transfer device 57 includes a transfer plate 58 including a main conveying portion 59, first and second transfer portions 61, 62 disposed on either side of the main conveying portion 59, and first and second secondary conveying portions 63, 64 disposed on either side of the first and second transfer portions 61, 62.

The transfer device 57 is displaceable between a conveying position (see FIG. 18) in which the first and second transfer portions 61, 62 partially define respectively the first and second guide tracks and the main conveying portion 59 partially defines the conveying track, a first transfer position (see FIG. 19) in which the first transfer portion 61 and the first secondary conveying portion 63 partially define respectively the second guide track and the conveying track, and a second transfer position in which the second transfer portion 62 and the second secondary conveying portion 64 partially define respectively the first guide track and the conveying track.

As shown in FIG. 1, the conveying system 3 includes a control unit 65 configured to wirelessly communicate, for example by WiFi or Bluetooth, with the self-propelled conveying carriage 25 and with the self-propelled loading carriage 39. The control unit 65 may consist of a computer, for example a PC-type computer. Advantageously, the control unit 65 is also configured to communicate with the different analysis and/or measurement stations 5.

Advantageously, the control means belonging to the self-propelled conveying carriage 25 are configured to receive control signals originating from the control unit 65, and to transmit drive signals in particular to the translational drive mechanism 28 and to the rotational drive mechanism 28 and to the actuation device, in response to the received control signals.

Figure 9:
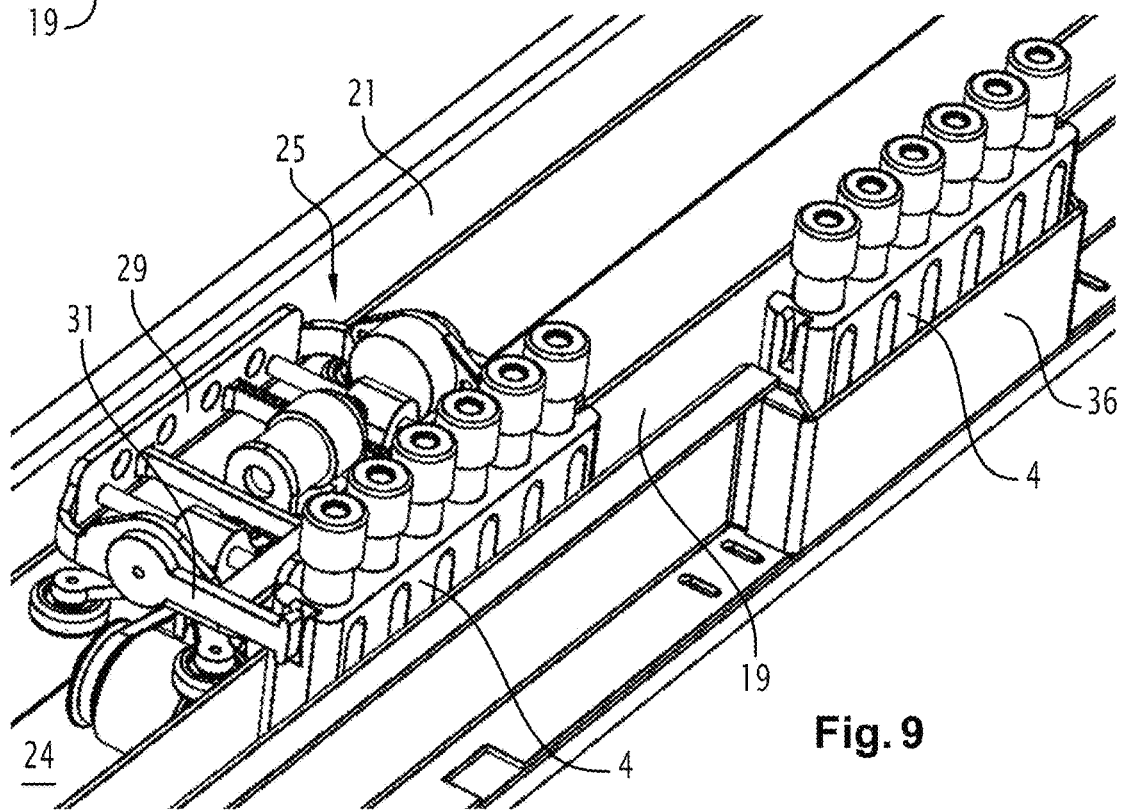

An example of a samples analysis method that may be carried out using the previously-described automatic analysis system 2 will now be described. Such a samples processing method comprises in particular the following steps consisting in:

a) manually loading a plurality of containers supports 4 in the loading area 17;

b) controlling a displacement of the self-propelled loading carriage 39 substantially vertically to a containers support 4, and controlling a translational displacement of the drive element 44 of the self-propelled loading carriage 39 into the drive position (see FIG. 10);

c) displacing the self-propelled loading carriage 39 toward the conveying unit 16 so as to automatically load a containers support 4 in the first guide track (see FIG. 12);

d) optically read, using the identification code reading device 51, the identification codes borne by the different containers 6 supported by the containers support 4 loaded in the first guide track and located opposite the loading area 17;

e) optionally, driving one or more of the container(s) 6 carried by the containers support 4 in rotation so as to enable the optical reading of their identification codes by the identification code reading device 51;

f) determining the conveying destinations of the containers support 4 loaded in the first guide track and located opposite the loading area 17 according to the identification codes borne by the different containers 6 supported by said containers support 4, and assigning said containers support 4 to an analysis and/or measurement station 5;

g) controlling a displacement of the self-propelled conveying carriage 25 opposite the loading area 17 (see FIG. 14), and a controlling a pivoting of the drive element 31 of the self-propelled conveying carriage 25 into the drive position so as to grasp the containers support 4;

h) controlling a displacement of the self-propelled conveying carriage 25 opposite a sampling area 36 associated to the analysis and/or measurement station 5 to which said containers support 4 is assigned (see FIG. 7), and controlling a translation of the support element 29 of the self-propelled conveying carriage 25 into the first or second clearance position (depending on the analysis and/or measurement station 5 to which the containers support 4 is assigned) so as to displace the containers support into the sampling area 36 (see FIG. 8);

i) controlling a pivoting of the drive element 31 of the self-propelled conveying carriage 25 into the release position so as to release the containers support 4;

j) collecting a sample in one or several container(s) 6 supported by said containers support 4, using the sampling device belonging to the analysis and/or measurement station 5 associated to the sampling area 36, and processing the collected sample(s) using the analysis and/or measurement station; during these sampling and processing steps, the self-propelled conveying carriage 25 may be controlled to displace one or several other containers support(s) 5 concurrently (see FIG. 9);

k) controlling a displacement of the self-propelled conveying carriage 25 opposite the sampling area 36, controlling a translation of the support element 29 of the self-propelled conveying carriage 25 into the first or second clearance position (depending on the analysis and/or measurement station 5 to which the containers support 4 is assigned), and controlling a pivoting of the drive element 31 of the self-propelled conveying carriage 25 into the drive position so as to grasp the containers support 4 received in the sampling area 36;

l) controlling a translation of the support element 29 of the self-propelled conveying carriage 25 into the conveying position so as to displace the containers support 4 in the first or second guide tracks (depending on the analysis and/or measurement station 5 to which the containers support 4 is assigned), m) controlling a displacement of the self-propelled conveying carriage 25 opposite the unloading area 18 (see FIG. 15), and controlling a translation of the support element 29 of the self-propelled conveying carriage 25 into the second clearance position so as to unload the containers support 4 in the unloading area 18 (see FIG. 16);

n) controlling a pivoting of the drive element 31 of the self-propelled conveying carriage 25 into the release position so as to release the containers support 4.

It should be noted that steps a) to f) may be carried out for a containers support 4 when the self-propelled conveying carriage 25 displaces another containers support 4. Thus, steps a) to f) may be carried out concurrently.

In order to increase the cadence of the conveying system 3, the latter may advantageously comprise several loading areas 17 disposed adjacent to each other, and several unloading areas 18 disposed adjacent to each other.

Such an analysis method may further comprise a step carried out between steps h and h) and consisting in transferring the containers support 4 from the first guide track into the second guide track using the transfer device 57 if the analysis and/or measurement station 5 to which the containers support 4 is assigned is disposed along the second guide track.

It should be further noted that the analysis system according to the present invention is intended to fluidify the samples processing flow in an analysis laboratory, in order to increase productivity and quality (reduction of the workforce and of errors). Thus, it goes without saying that the conveying system according to the invention is configured to communicate with the control unit 65, which manages the workloads of the different analysis and/or measurement stations 5 (such as the tests to perform for each sample), and transmit them to the conveying system 3 and to the analysis and/or measurement stations 5 so that the different containers 6 are conveyed toward the analysis and/or measurement stations 5 according to the tests requests and the capacities of each analysis and/or measurement station 5. Hence, the control unit 65, which manages the conveying and loading carriages, features an «intelligence», a kind of ERP (integrated management software) for optimizing the conveyances of the containers supports 4 according to the workloads of the different analysis and/or measurement stations 5.

It should be further noted that each analysis and/or measurement station 5 may comprise a communication and visualization interface, and embedded electronics (not represented in the figures). For example, each communication and visualization interface includes a tactile screen 66 connected to a PC-type computer. More particularly, the PC-type computer is arranged to save analysis requests manually loaded by an operator using the tactile screen or originating from the control unit 65, send analysis requests to the embedded electronics, retrieve measured data, process them thanks to specific algorithms, and deliver the results to the operator or transmit them to the control unit 65.

According to an embodiment of the invention, at least one of the analysis and/or measurement stations 5 may be replaced with an analysis device as described in the document FR2998057. According to such an embodiment, the respective sampling area 36 is replaced with a transfer area enabling a transfer of a containers support 4 from the respective guide track toward the analysis device.

It goes without saying that the invention is not limited to the sole embodiment of this conveying system, described hereinabove as example, but it comprises on the contrary all variants thereof.

What is claimed is:

1. A conveying system configured to convey containers supports intended to support containers containing samples of a biological liquid, the conveying system including at least:
   a support guide element defining a guide track, the support guide element being configured to receive a containers support and guide said containers support in translation along the guide track, the support guide element including a first bottom surface,
   a carriage guide element extending along the support guide element and defining a conveying track, the carriage guide element including a second bottom surface, the carriage guide element and the support guide element extending side by side, the first bottom surface and the second bottom surface extending in a common horizontal plane, and
   a self-propelled conveying carriage configured to be received on the carriage guide element and configured to be guided by the carriage guide element during displacements of the self-propelled conveying carriage along the conveying track, the self-propelled conveying carriage comprising a drive element movably mounted between at least a drive position in which the drive element is configured to transmit a drive movement to the containers support received on the support guide element and located alongside the self-propelled conveying carriage, and a release position in which the drive element is configured to release the containers support, the self-propelled conveying carriage being configured to displace the containers support in translation along the guide track when the drive element is in the drive position and the self-propelled conveying carriage is displaced along the conveying track,
   wherein the self-propelled conveying carriage includes a carriage body and a support element on which the drive element is movably mounted, the support element being mounted movable in translation relative to the carriage body between at least a conveying position and a clearance position and according to a direction of displacement which is horizontal and perpendicular to the conveying track.

2. The conveying system according to claim 1, wherein the drive element is pivotally mounted about a pivot axis.

3. The conveying system according to claim 1, wherein the drive element includes two drive branches spaced from each other and configured to cooperate with the containers support when the drive element is in the drive position.

4. The conveying system according to claim 1, wherein the self-propelled conveying carriage includes at least one drive wheel, and at least one rotational drive mechanism configured to drive the at least one drive wheel in rotation.

5. The conveying system according to claim 1, wherein the self-propelled conveying carriage includes guide rollers configured to cooperate with the carriage guide element during the displacements of the self-propelled conveying carriage along the conveying track.

6. The conveying system according to claim 1, which comprises at least one sampling or transfer area disposed along the guide track and outside the guide track, and wherein the self-propelled conveying carriage is configured to displace the containers support, received on the support guide element, into the at least one sampling or transfer area so as to release the guide track.

7. The conveying system according to claim 6, wherein the at least one sampling or transfer area includes a sampling location arranged to receive and store at least temporarily the containers support.

8. The conveying system according to claim 1, wherein the support element includes a pushing surface configured to exert a pushing force against the containers support when the containers support is received on the first support guide element and the support element is displaced toward the clearance position.

9. The conveying system according to claim 1, which comprises a loading area intended to store the containers support and comprising a loading device arranged to load the containers support in the guide track defined by the support guide element, and an unloading area in which the containers support is intended to be unloaded.

10. The conveying system according to claim 1, which includes an identification code reading device configured to optically read identification codes borne by containers supported by the containers support when the containers support is received on the support guide element.

11. The conveying system according to claim 10, which comprises a rotational drive module configured to drive containers supported by the containers support in rotation when the containers support is received on the support guide element, so as to enable the reading of the identification codes borne by said containers by the identification code reading device.

12. The conveying system according to claim 1, which includes a control unit configured to remotely communicate with the self-propelled conveying carriage.

13. The conveying system according to claim 1, which includes a storage rotor with a substantially vertical axis of rotation, the storage rotor including a plurality of storage housings each configured to receive a containers support coming from the guide track.

14. An automatic analysis system for in vitro diagnosis, comprising a conveying system according to claim 1, and at least one samples processing station disposed along the guide track.

15. A conveying system configured to convey containers supports intended to support containers containing samples of a biological liquid, the conveying system including at least:
- a containers support track which is configured to receive a containers support and along which said containers support is displaceable,
- a carriage guide element extending along the containers support track and defining a conveying track, the containers support track and the conveying track extending side by side in a common horizontal plane, and
- a self-propelled conveying carriage configured to be received on the carriage guide element and configured to be guided by the carriage guide element during displacements of the self-propelled conveying carriage along the conveying track, the self-propelled conveying carriage comprising a drive element movably mounted between at least a drive position in which the drive element is configured to transmit a drive movement to the containers support received in the containers support track and located alongside the self-propelled conveying carriage, and a release position in which the drive element is configured to release the containers support, the self-propelled conveying carriage being configured to displace the containers support along the containers support track when the drive element is in the drive position and the self-propelled conveying carriage is displaced along the conveying track,
wherein the self-propelled conveying carriage includes a carriage body and a support element on which the drive element is movably mounted, the support element being mounted movable in translation relative to the carriage body between at least a conveying position and a clearance position and according to a direction of displacement which is horizontal and perpendicular to the conveying track.

* * * * *